US009687477B2

(12) United States Patent
Hahm et al.

(10) Patent No.: US 9,687,477 B2
(45) Date of Patent: Jun. 27, 2017

(54) MODULATION OF SPHINGOSINE 1-PHOSPHATE METABOLIZING ENZYMES FOR THE TREATMENT OF NEGATIVE-STRAND RNA VIRUS INFECTIONS

(75) Inventors: Bumsuk Hahm, Columbia, MO (US); Young-Jin Seo, Atlanta, GA (US); Stephen Alexander, Columbia, MO (US); Vijayan Madhuvanthi, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 475 days.

(21) Appl. No.: 14/122,399

(22) PCT Filed: May 31, 2012

(86) PCT No.: PCT/US2012/040115
§ 371 (c)(1),
(2), (4) Date: Aug. 28, 2014

(87) PCT Pub. No.: WO2012/166859
PCT Pub. Date: Dec. 6, 2012

(65) Prior Publication Data
US 2015/0126564 A1 May 7, 2015

Related U.S. Application Data

(60) Provisional application No. 61/519,881, filed on Jun. 1, 2011.

(51) Int. Cl.
*A61K 31/425* (2006.01)
*A01N 43/78* (2006.01)
*A61K 31/426* (2006.01)
*A61K 31/133* (2006.01)
*C12N 9/88* (2006.01)
*C12N 15/113* (2010.01)
*A61K 48/00* (2006.01)

(52) U.S. Cl.
CPC .......... *A61K 31/426* (2013.01); *A61K 31/133* (2013.01); *C12N 9/88* (2013.01); *C12N 15/113* (2013.01); *C12N 15/1137* (2013.01); *C12N 15/1138* (2013.01); *C12Y 401/02027* (2013.01); *A61K 48/005* (2013.01); *C12N 2310/14* (2013.01); *C12N 2760/16111* (2013.01); *C12N 2760/18411* (2013.01)

(58) Field of Classification Search
CPC .. A61K 31/133; A61K 31/426; A61K 48/005; C12Y 401/02027; C12N 15/113; C12N 15/1137; C12N 15/1138; C12N 2310/14; C12N 2760/16111; C12N 2760/18411; C12N 9/88
USPC ................... 514/370, 669; 548/193; 564/506
See application file for complete search history.

(56) References Cited

U.S. PATENT DOCUMENTS

| | | | | |
|---|---|---|---|---|
| 8,629,383 B2* | 1/2014 | Beardsworth | ............... | F24J 2/38 126/572 |
| 2005/0277612 A1* | 12/2005 | Merchiers | .......... | C12N 15/1137 514/44 A |
| 2009/0312291 A1 | 12/2009 | Kawakami | | |
| 2010/0137315 A1* | 6/2010 | Smith | .................... | C07C 233/75 514/236.8 |

FOREIGN PATENT DOCUMENTS

WO 2012166859 A3 12/2012

OTHER PUBLICATIONS

Seo, Y. J., et al., Sphingosine 1-phosphate-metabolizing enzymes control influenza virus propagation and viral cytopathogenicity. J. Virol. 84(16): 8124-8131 (Epub. Jun. 2, 2010).
Monick, M. M., et al., Sphingosine kinase mediates activation of extracellular signal-related kinase and Akt by respiratory syncytial virus. Am. J. Respir. Cell Mol. Biol. 30(6): 844-852 (Epub. Jan. 23, 2004).
Palese, P., et al. , Negative-strand RNA viruses: genetic engineering and applications. Proc. Nat l. Acad. Sci. U. S. A. 93(21): 11354-11358 (15oct. 1996).
Stow, D. L., et al., Sphingosine kinase localization in the control of sphingolipid metabolism. Adv. Enzyme Regul. 51(1): 229-244 (Epub. Nov. 12, 2010).
Beljanski, V., C. Knaak, Y. Zhuang, and C. D. Smith. 2011. Combined anticancer effects of sphingosine kinase inhibitors and sorafenib. Invest New Drugs 29:1132-42.
Buehrer, B. M., and R. M. Bell. 1992. Inhibition of sphingosine kinase in vitro and in platelets. Implications for signal transduction pathways. J Biol Chem 267:3154-9.
Claas, E. C., A. D. Osterhaus, R. Van Beek, J. C. De Jong, G. F. Rimmelzwaan, D. A. Senne, S. Krauss, K. F. Shortridge, and R. G. Webster. 1998. Human influenza A H5N1 virus related to a highly pathogenic avian influenza virus. Lancet 351:472-7.

(Continued)

*Primary Examiner* — My-Chau T Tran
(74) *Attorney, Agent, or Firm* — The Intellectual Property Office of Verne A. Luckow, LLC

(57) ABSTRACT

The present invention relates to compounds and methods for the prevention or treatment of infections by negative strand RNA viruses, such as influenza virus and measles virus, wherein said compounds delay or inhibit viral replication by modulating the level or activity of a polypeptide involved in the synthesis or degradation of sphingosine-1-phosphate (S1P) in a cell, tissue, or subject. The methods involve administration of one or more compounds which modulate the level of gene expression, where the gene encodes a polypeptide involved in regulating the metabolic level of S1P, or modulate the level or activity of a polypeptide involved in regulating the metabolic level of S1P, such as sphingosine kinase (SK) and S1P lyase (SPL). Exemplary methods are directed towards reducing the level of SW by reducing the level or activity of one or more SKs, increasing the level or activity of one or more SPLs, or a combination of both steps.

30 Claims, 13 Drawing Sheets

(56) References Cited

OTHER PUBLICATIONS

Cyster, J. G. 2005. Chemokines, sphingosine-1-phosphate, and cell migration in secondary lymphoid organs. Annu Rev Immunol 23:127-59.

David, M., E. Petricoin, 3rd, C. Benjamin, R. Pine, M. J. Weber, and A. C. Larner. 1995. Requirement for MAP kinase (ERK2) activity in interferon alpha- and interferon beta-stimulated gene expression through STAT proteins. Science 269:1721-3.

Dharan, N. J., L. V. Gubareva, J. J. Meyer, M. Okomo-Adhiambo, R. C. McClinton, S. A. Marshall, K. St George, S. Epperson, L. Brammer, A. I. Klimov, J. S. Bresee, and A. M. Fry. 2009. Infections with oseltamivir-resistant influenza A(H1N1) virus in the United States. JAMA 301:1034-41.

Edsall, L. C., J. R. Van Brocklyn, O. Cuvillier, B. Kleuser, and S. Spiegel. 1998. N,N-Dimethylsphingosine is a potent competitive inhibitor of sphingosine kinase but not of protein kinase C: modulation of cellular levels of sphingosine 1-phosphate and ceramide. Biochemistry 37:12892-8.

Fraser, C., C. A. Donnelly, S. Cauchemez, W. P. Hanage, M. D. Van Kerkhove, T. D. Hollingsworth, J. Griffin, R. F. Baggaley, H. E. Jenkins, E. J. Lyons, T. Jombart, W. R. Hinsley, N. C. Grassly, F. Balloux, A. C. Ghani, N. M. Ferguson, A. Rambaut, O. G. Pybus, H. Lopez-Gatell, C. M. Alpuche-Aranda, I. B. Chapela, E. P. Zavala, D. M. Guevara, F. Checchi, E. Garcia, S. Hugonnet, and C. Roth. 2009. Pandemic potential of a strain of influenza A (H1N1): early findings. Science 324:1557-61.

French, K. J., R. S. Schrecengost, B. D. Lee, Y. Zhuang, S. N. Smith, J. L. Eberly, J. K. Yun, and C. D. Smith. 2003. Discovery and evaluation of inhibitors of human sphingosine kinase. Cancer Res 63:5962-9.

French, K. J., Y. Zhuang, L. W. Maines, P. Gao, W. Wang, V. Beljanski, J. J. Upson, C. L. Green, S. N. Keller, and C. D. Smith. 2010. Pharmacology and antitumor activity of ABC294640, a selective inhibitor of sphingosine kinase-2. J Pharmacol Exp Ther 333:129-39.

Garcia-Sastre, A., R. K. Durbin, H. Zheng, P. Palese, R. Gertner, D. E. Levy, and J. E. Durbin. 1998. The role of interferon in influenza virus tissue tropism. J Virol 72:8550-8.

Horga, A., and X. Montalban. 2008. FTY720 (fingolimod) for relapsing multiple sclerosis. Expert Rev Neurother 8:699-714.

Kash, J. C., T. M. Tumpey, S. C. Proll, V. Carter, O. Perwitasari, M. J. Thomas, C. F. Basler, P. Palese, J. K. Taubenberger, A. Garcia-Sastre, D. E. Swayne, and M. G. Katze. 2006. Genomic analysis of increased host immune and cell death responses induced by 1918 influenza virus. Nature 443:578-81.

Lin, C., R. E. Holland, Jr., J. C. Donofrio, M. H. McCoy, L. R. Tudor, and T. M. Chambers. 2002. Caspase activation in equine influenza virus induced apoptotic cell death. Vet Microbiol 84:357-65.

Lindsay, M. E., J. M. Holaska, K. Welch, B. M. Paschal, and I. G. Macara. 2001. Ran-binding protein 3 is a cofactor for Crm1-mediated nuclear protein export. J Cell Biol 153:1391-402.

Maines, L. W., L. R. Fitzpatrick, K. J. French, Y. Zhuang, Z. Xia, S. N. Keller, J. J. Upson, and C. D. Smith. 2008. Suppression of ulcerative colitis in mice by orally available inhibitors of sphingosine kinase. Dig Dis Sci 53:997-1012.

Marsolais, D., B. Hahm, K. H. Edelmann, K. B. Walsh, M. Guerrero, Y. Hatta, Y. Kawaoka, E. Roberts, M. B. Oldstone, and H. Rosen. 2008. Local not systemic modulation of dendritic cell S1P receptors in lung blunts virus-specific immune responses to influenza. Mol Pharmacol 74:896-903.

Marsolais, D., B. Hahm, K. B. Walsh, K. H. Edelmann, D. McGavern, Y. Hatta, Y. Kawaoka, H. Rosen, and M. B. Oldstone. 2009. A critical role for the sphingosine analog AAL-R in dampening the cytokine response during influenza virus infection. Proc Natl Mad Sci U S A 106:1560-5.

McLean, J. E., E. Datan, D. Matassov, and Z. F. Zakeri. 2009. Lack of Bax prevents influenza A virus-induced apoptosis and causes diminished viral replication. J Virol 83:8233-46.

Min, J., A. Mesika, M. Sivaguru, P. P. Van Veldhoven, H. Alexander, A. H. Futerman, and S. Alexander. 2007. (Dihydro)ceramide synthase 1 regulated sensitivity to cisplatin is associated with the activation of p38 mitogen-activated protein kinase and is abrogated by sphingosine kinase 1. Mol Cancer Res 5:801-12.

Min, J., P. P. Van Veldhoven, L. Zhang, M. H. Hanigan, H. Alexander, and S. Alexander. 2005. Sphingosine-1-phosphate lyase regulates sensitivity of human cells to select chemotherapy drugs in a p38-dependent manner. Mol Cancer Res 3:287-96.

Mok, C. K., D. C. Lee, C. Y. Cheung, M. Peiris, and A. S. Lau. 2007. Differential onset of apoptosis in influenza A virus H5N1- and H1N1-infected human blood macrophages. J Gen Virol 88:1275-80.

Molinari, N. A., I. R. Ortega-Sanchez, M. L. Messonnier, W. W. Thompson, P. M. Wortley, E. Weintraub, and C. B. Bridges. 2007. The annual impact of seasonal influenza in the US: measuring disease burden and costs. Vaccine 25:5086-96.

Morens, D. M., and A. S. Fauci. 2007. The 1918 influenza pandemic: insights for the 21st century. J Infect Dis 195:1018-28.

Olivera, A., T. Kohama, L. Edsall, V. Nava, O. Cuvillier, S. Poulton, and S. Spiegel. 1999. Sphingosine kinase expression increases intracellular sphingosine-1-phosphate and promotes cell growth and survival. J Cell Biol 147:545-58.

Oskouian, B., P. Sooriyakumaran, A. D. Borowsky, A. Crans, L. Dillard-Telm, Y. Y. Tam, P. Bandhuvula, and J. D. Saba. 2006. Sphingosine-1-phosphate lyase potentiates apoptosis via p53- and p38-dependent pathways and is down-regulated in colon cancer. Proc Nati Acad Sci U S A 103:17384-9.

Park, Y. S., S. Hakomori, S. Kawa, F. Roan, and Y. Igarashi. 1994. Liposomal N,N,N-trimethylsphingosine (TMS) as an inhibitor of B16 melanoma cell growth and metastasis with reduced toxicity and enhanced drug efficacy compared to free TMS: cell membrane signaling as a target in cancer therapy III. Cancer Res 54:2213-7.

Paugh, S. W., B. S. Paugh, M. Rahmani, D. Kapitonov, J. A. Almenara, T. Kordula, S. Milstien, J. K. Adams, R. E. Zipkin, S. Grant, and S. Spiegel. 2008. A selective sphingosine kinase 1 inhibitor integrates multiple molecular therapeutic targets in human leukemia. Blood 112:1382-91.

Rosen, H., and E. J. Goetzl. 2005. Sphingosine 1-phosphate and its receptors: an autocrine and paracrine network. Nat Rev Immunol 5:560-70.

Spiegel, S., and R. Kolesnick. 2002. Sphingosine 1-phosphate as a therapeutic agent. Leukemia 16:1596-602.

Takizawa, T., S. Matsukawa, Y. Higuchi, S. Nakamura, Y. Nakanishi, and R. Fukuda. 1993. Induction of programmed cell death (apoptosis) by influenza virus infection in tissue culture cells. J Gen Virol 74 (Pt 11):2347-55.

Tewari, M., L. T. Quan, K. O'Rourke, S. Desnoyers, Z. Zeng, D. R. Beidler, G. G. Poirier, G. S. Salvesen, and V. M. Dixit. 1995. Yama/CPP32 beta, a mammalian homolog of CED-3, is a CrmA-inhibitable protease that cleaves the death substrate poly(ADP-ribose) polymerase. Cell 81:801-9.

Thompson, W. W., D. K. Shay, E. Weintraub, L. Brammer, C. B. Bridges, N. J. Cox, and K. Fukuda. 2004. Influenza-associated hospitalizations in the United States. JAMA 292:1333-40.

Wong, L., S. S. Tan, Y. Lam, and A. J. Melendez. 2009. Synthesis and evaluation of sphingosine analogues as inhibitors of sphingosine kinases. J Med Chem 52:3618-26.

Wurzer, W. J., O. Planz, C. Ehrhardt, M. Giner, T. Silberzahn, S. Pleschka, and S. Ludwig. 2003. Caspase 3 activation is essential for efficient influenza virus propagation. EMBO J 22:2717-28.

Yatomi, Y., F. Ruan, T. Megidish, T. Toyokuni, S. Hakomori, and Y. Igarashi. 1996. N,N-dimethylsphingosine inhibition of sphingosine kinase and sphingosine 1-phosphate activity in human platelets. Biochemistry 35:626-33.

Moon, S. O., S. Shin, Y. Liu, B. A. Ballif, M. S. Woo, S. P. Gygi, and J. Blenis. 2008. Ran-binding protein 3 phosphorylation links the Ras and PI3-kinase pathways to nucleocytoplasmic transport. Mol Cell 29:362-75.

* cited by examiner

Preferential activation of ERK, but not p38, Akt, and JNK in SPL cells

Enhanced susceptibility of SK1 cells to influenza virus infection

Reduced mortality of influenza virus-infected mice by SK inhibitor treatment

Suppression of measles virus replication by SK inhibitor

■ CTR
■ SKI-II (5 μM)
□ SKI-II (10 μM)

FIG. 13

```
SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Artificial sequence - PCR primer IFN-fwd used
      to amplify segment of interferon gene

<400> SEQUENCE: 1
cgccgcattg accatcta                                                  18

<210> SEQ ID NO 2
<211> LENGTH: 22
<212> TYPE: DNA
<213> ORGANISM: Artificial Sequence
<220> FEATURE:
<223> OTHER INFORMATION: Artificial sequence - PCR primer IFN-rev used
      to amplify segment of interferon gene

<400> SEQUENCE: 2
gacattagcc aggaggttct ca                                             22

<210> SEQ ID NO 3
<211> LENGTH: 18
<212> TYPE: DNA
<213> ORGANISM: Artificial Sequence
<220> FEATURE:
<223> OTHER INFORMATION: Artificial sequence - PCR primer GAPDH-fwd used
      to amplify segment of GAPDH gene

<400> SEQUENCE: 3
tcaccaccat ggagaagg                                                  18

<210> SEQ ID NO 4
<211> LENGTH: 20
<212> TYPE: DNA
<213> ORGANISM: Artificial Sequence
<220> FEATURE:
<223> OTHER INFORMATION: Artificial sequence - PCR primer GAPDH-rev used
      to amplify segment of GAPDH gene

<400> SEQUENCE: 4
gataagcagt tggtggtgca                                                20
```

```
<210> SEQ ID NO 5
<211> LENGTH: 21
<212> TYPE: DNA
<213> ORGANISM: Artificial Sequence
<220> FEATURE:
<223> OTHER INFORMATION: Artificial sequence - PCR primer SK1-fwd used
      to amplify segment of SK1 gene

<400> SEQUENCE: 5
tgtgaaccac tatgctgggt a                                                 21

<210> SEQ ID NO 6
<211> LENGTH: 18
<212> TYPE: DNA
<213> ORGANISM: Artificial Sequence
<220> FEATURE:
<223> OTHER INFORMATION: Artificial sequence - PCR primer SK1-rev used
      to amplify segment of SK1 gene

<400> SEQUENCE: 6
cagcccagaa gcagtgtg                                                     18

<210> SEQ ID NO 7
<211> LENGTH: 19
<212> TYPE: DNA
<213> ORGANISM: Artificial Sequence
<220> FEATURE:
<223> OTHER INFORMATION: Artificial sequence - PCR primer SK2-fwd used
      to amplify segment of SK2 gene

<400> SEQUENCE: 7
agacgggctg ctttacgag                                                    19

<210> SEQ ID NO 8
<211> LENGTH: 18
<212> TYPE: DNA
<213> ORGANISM: Artificial Sequence
<220> FEATURE:
<223> OTHER INFORMATION: Artificial sequence - PCR primer SK2-rev used
      to amplify segment of SK2 gene

<400> SEQUENCE: 8
caggggagga caccaatg                                                     18
```

MODULATION OF SPHINGOSINE 1-PHOSPHATE METABOLIZING ENZYMES FOR THE TREATMENT OF NEGATIVE-STRAND RNA VIRUS INFECTIONS

CROSS REFERENCE TO RELATED APPLICATIONS

The application claims priority under 35 U.S.C. §119(e) to U.S. Provisional Patent Application No. 61/519,881, filed Jun. 1, 2011, and priority under 35 U.S.C. 371 to PCT/US12/40115, filed May 31, 2012, the disclosures of which are incorporated herein by reference.

STATEMENT REGARDING FEDERALLY-SPONSORED RESEARCH OR DEVELOPMENT

This invention was made with Government support under Grants No. AI088363 and AI091797 awarded by the National Institutes of Health. The Government has certain rights in the invention.

INCORPORATION-BY-REFERENCE OF A SEQUENCE LISTING

The sequence listing contained in the file "127185_0008_US_Sequence_Listing_ST25.txt", created on Nov. 26, 2013, modified on Nov. 26, 2013, file size 2,620 bytes, is incorporated by reference in its entirety herein.

FIELD OF THE INVENTION

The present invention relates to compounds and methods for the prevention or treatment of infections by negative-strand RNA viruses, such as influenza virus and measles virus, wherein said compounds delay or inhibit viral replication by modulating the level or activity of a polypeptide involved in the synthesis or degradation of sphingosine-1-phosphate (S1P) in a cell, tissue, or subject. The methods involve administration of one or more compounds which modulate the level of gene expression, where the gene encodes a polypeptide involved in regulating the metabolic level of S1P, or modulate the level or activity of a polypeptide involved in regulating the metabolic level of S1P, such as sphingosine kinase (SK) and S1P lyase (SPL). Exemplary methods are directed towards reducing the level of S1P by reducing the level or activity of one or more SKs, increasing the level or activity of one or more SPLs, or a combination of both steps.

BACKGROUND OF THE INVENTION

Influenza virus belongs to the family Orthomyxoviridae and the viral genome is formed by eight segments of negative-sense, single-stranded RNAs. Influenza virus is a major health concern and significant economic burden throughout the world (23). In the United States, influenza infections are responsible for over 200,000 hospitalizations, and an average of 36,000 deaths every year (33). Fear of a devastating influenza pandemic, similar to the Spanish influenza pandemic in 1918/1919 which killed 40-50 million people worldwide, has also been increased in recent years (24). On Jun. 11, 2009, the World Health Organization (WHO) declared the spread of the 2009 influenza A (H1N1) virus (initially known as Swine Flu) as a global influenza pandemic (8). Outbreaks of avian H5N1 influenza increased awareness and elevated vigilance against the occurrence of an influenza pandemic (3). Many strains of circulating seasonal influenza viruses, and strains of the avian H5N1 influenza virus with pandemic potential, were found to be resistant to anti-viral drugs, amplifying health care concerns (6). Identifying new therapeutic targets and understanding the mechanisms of host-virus interactions are important biomedical goals.

Sphingolipids are bioactive lipid mediators characterized by the presence of a serine head group with one or two fatty acid tails (4). Sphingosine, and its downstream product sphingosine 1-phosphate (S1P), have emerged as the modulators of multiple cellular processes, such as cell growth, survival, differentiation, and cell migration, and are being investigated as potential leads for the development of therapeutic agents. One example is the sphingosine analog FTY720, which was recently approved for the treatment of multiple sclerosis by the FDA as an orally-administrable drug (12). S1P that is generated inside cells can trigger intracellular signaling pathways, and S1P that is secreted can act as an exogenous lipid mediator, stimulating S1P receptor-mediated signaling pathways (29).

The level of S1P is tightly regulated by a variety of S1P-metabolizing enzymes, including sphingosine kinases (SK) and S1P lyases (SPL). Synthesis of S1P from sphingosine is catalyzed by SK, while SPL catalyzes the degradation of S1P to phosphoethanolamine and hexadecanal (30). These S1P-metabolizing enzymes were revealed to modulate diverse cellular stresses induced by anti-cancer drugs (20), DNA damage (26), or serum deprivation (25). Cells overexpressing sphingosine kinase 1 (SK1) displayed increased resistance to a variety of anti-cancer drugs, such as cisplatin, carboplatin, and doxorubicin (20), and cells overexpressing SPL were shown to be more sensitive to drug-mediated cell death (21).

A phosphorylated sphingosine analog, AAL-R, was recently shown to display immunomodulatory activity to alleviate influenza virus-induced immune pathology (17, 18). This analog acted directly on S1P receptors to regulate the expression of inflammatory cytokines, although it did not significantly alter the propagation of influenza virus (18). The role of intracellular S1P-metabolizing enzymes in host cellular defense mechanisms that target viral infections has not been previously studied in any great detail.

In view of these observations, there is a need to provide new and improved methods for the prevention or treatment of viral infections, by targeting cellular processes required for viral replication that can be inhibited or delayed by modulating the level or activity of polypeptides involved in metabolism of S1P and similar lipid mediators.

BRIEF SUMMARY OF THE INVENTION

One aspect of the invention relates to a method of modulating the infection, replication, assembly, or release of a negative-strand RNA virus in a eukaryotic cell, comprising administering one or more agents which modulate the level or activity of a protein involved in the synthesis or degradation of sphingosine-1-phosphate in said cell.

Another aspect relates to a composition for modulating the infection, replication, assembly, or release of a negative-strand RNA virus in a eukaryotic cell, comprising an effective amount of an S1P-modulating agent, wherein the S1P-modulating agent decreases the level of S1P within said cell in a sample of cells contacted with the S1P-modulating agent compared to control sample of cells not contacted with the S1P-modulating agent.

Another aspect relates to a method for treating, preventing, or ameliorating one or more symptoms associated with a negative-strand RNA virus infection in a subject, said method comprising administering to a subject in need thereof, a prophylactically- or therapeutically-effective amount of one or more agents which modulate the level or activity of a polypeptide involved in the synthesis or degradation of sphingosine-1-phosphate in said subject.

A better understanding of the disclosed compounds and methods can be obtained from the following detailed descriptions and accompanying drawings, which set forth illustrative examples indicative of the various ways in which aspects of the disclosed subject matter may be used and appreciated.

BRIEF DESCRIPTION OF THE DRAWINGS

The foregoing aspects and many of the advantages of this disclosure are more readily appreciated as the same become better understood by reference to the following detailed description, when taken in conjunction with the accompanying drawings, wherein:

FIG. 8 (Panels A-B) set forth data illustrating reduced mortality of influenza virus-infected mice by SK inhibitor treatment. (A) Wild-type C57BL/6 mice (n=5/group) were infected in vivo with influenza virus at $10^5$ plaque forming unit (PFU) intra-nasally (i.n.) and injected with vehicle (control, CTR) or DMS {0.1 mg/kg (mpk)} and their lifespan was monitored. (B) Mice were infected with $5 \times 10^4$ PFU of influenza virus and then treated with vehicle (control, CTR), DMS (0.003 mpk) or SKI-II (0.012 mpk) via intra-nasal inoculation. Survival of the infected mice was monitored daily for 14 days.

FIG. 13 sets forth data illustrating suppressive activity of SK inhibitor in measles virus replication. B95-8 cells were infected with measles virus at 1 MOI in the presence or absence of SKI-II (5 or 10 μM). At 2 or 3 dpi, viral titers were quantified by plaque assay.

Figure 1:
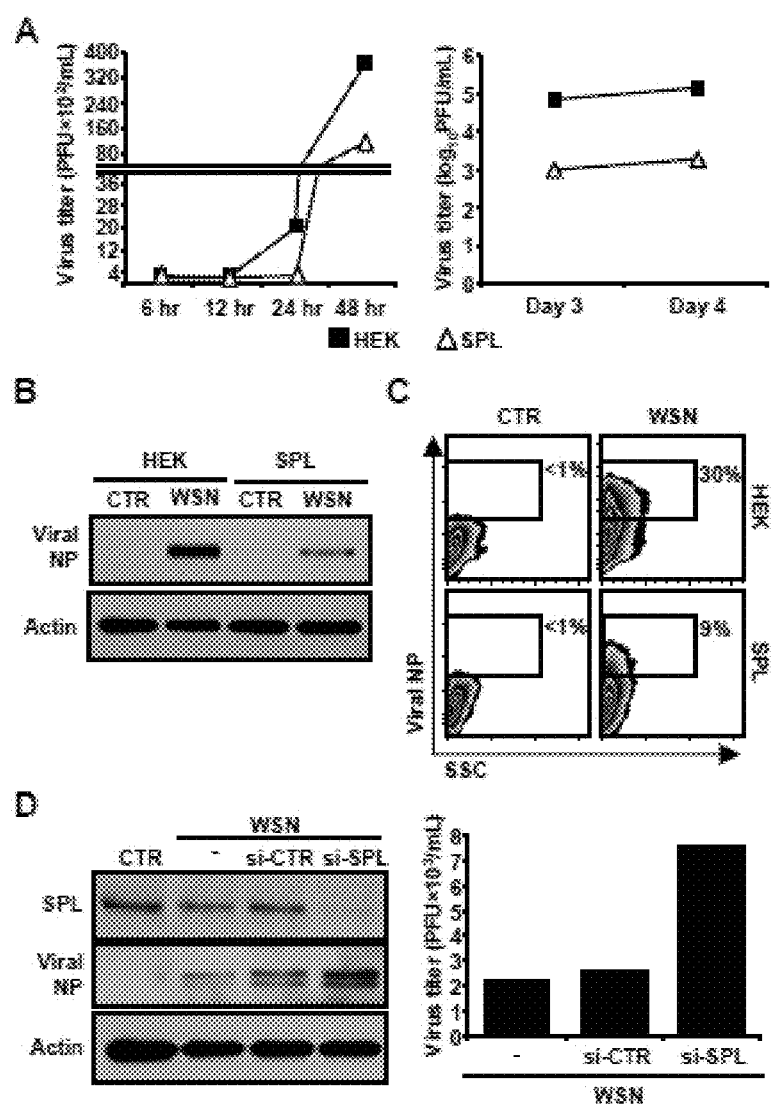
FIG. 1 (Panels A-D) set forth data illustrating the effect of SPL overexpression on influenza virus amplification. (A) Human embryonic kidney (HEK) 293 cells (HEK-cells) or SPL-overexpressing HEK293 cells (SPL-cells) were infected with influenza virus at 0.1 multiplicity of infection (MOI). At, 6, 12, 24 or 48 hpi (left panel), and 3 or 4 dpi (right panel), viral titers were determined by plaque assay. (B) HEK-cells or SPL-cells were uninfected (control, CTR) or infected with influenza virus at 1 MOI. At 2 dpi, influenza viral nucleoprotein (NP) and actin were detected by Western blot analysis. (C) Cells were uninfected (CTR) or infected with influenza virus at 0.1 MOI, and analyzed for the expression of viral NP by flow cytometry at 3 dpi. The percentiles of virus NP(+) cells are depicted. SSC, side scatter. (D) SPL-cells were mock-transfected (−), or transfected with control small interfering RNA (siRNA) (si-CTR) or siRNA targeting SPL (si-SPL), and then infected with influenza virus at 1 MOI. Uninfected SPL-cells are shown as CTR. At 2 dpi, Western blot analysis was performed to detect SPL, influenza viral NP and actin (left panel); viral titers were quantified by plaque assay (right panel).

Abbreviations and their corresponding meanings include: mg=milligram(s); mM=millimolar; PCR=polymerase chain reaction; RT=reverse transcriptase; RT=room temperature; SDS-PAGE=sodium dodecyl sulfate-polyacrylamide gel electrophoresis; U=units; μg=micro gram(s); μM micromolar; S1P=sphingosine-1-phosphate; SK=sphingosine kinase; SPL=S1P lyase; CTR=control; VEH=vehicle; DMS=D-erythro-N,N-dimethylsphingosine; HEK=human embryonic kidney; MDCK=Madin-Darby Canine Kidney; $EC_{50}$=50% effective concentration; FDA=food and drug Administration; MOI=multiplicity of infection; PFU=plaque forming unit; mpk=milligram per kilogram; SSC=side scatter; siRNA=small interfering RNA; dpi=day post-infection; hpi=hour post-infection; DMSO=dimethyl sulfoxide; IFN=interferon; CPE=cytopathic effect; NS=not significant; SEM=standard error of the mean; NP=nucleoprotein; NS1=nonstructural protein 1; PARP=poly (ADP-ribose) polymerase; Bcl-2=B-cell lymphoma 2; Bax=Bcl-2 associated X-protein; STAT=signal transducer and activator of transcription; JAK=janus kinase; ERK=extracellular-signal-regulated kinase; JNK=c-Jun NH2-terminal kinase; RanBP3=Ran binding protein 3; MAP=mitogen activated protein; RSK=ribosomal S6 kinase.

Unless otherwise defined, all other technical and scientific terms used herein have the same meaning as commonly understood by one of ordinary skill in the art in the field of the invention described herein.

DETAILED DESCRIPTION

One major aspect of the invention relates to a method of modulating the infection, replication, assembly, or release of a negative-strand RNA virus in a eukaryotic cell, comprising administering one or more agents which modulate the level or activity of a protein involved in the synthesis or degradation of sphingosine-1-phosphate in said cell.

Another major aspect relates to a composition for modulating the infection, replication, assembly, or release of a negative-strand RNA virus in a eukaryotic cell, comprising an effective amount of an S1P-modulating agent, wherein the S1P-modulating agent decreases the level of S1P within said cell in a sample of cells contacted with the S1P-modulating agent compared to control sample of cells not contacted with the S1P-modulating agent.

Another major aspect relates to a method for treating, preventing, or ameliorating one or more symptoms associated with a negative-strand RNA virus infection in a subject, said method comprising administering to a subject in need thereof, a prophylactically- or therapeutically-effective amount of one or more agents which modulate the level or activity of a polypeptide involved in the synthesis or degradation of sphingosine-1-phosphate in said subject.

Different negative-strand RNA viruses may be used in various aspects of the invention, including those in a family selected from the group consisting of Orthomyxoviridae and Paramyxoviridae. In one aspect, the family is Orthomyxoviridae, exemplified by influenza virus, and in another aspect, the family is Paramyxoviridae, exemplified by measles virus. Viruses having similar genetic characteristics, belonging to these or other virus families are also included in other aspects of the invention, e.g., Vesicular Stomatitis virus (Rhabdoviridae family), Newcastle disease virus and Parainfluenza virus (Paramyxoviridae family), Ebola virus and Marburg virus (Filoviridae family), Borna disease virus (Bornaviridae family), and Hantavirus (Bunyaviridae family).

In one aspect, at least one of said agents modulates the level of a nucleic acid encoding a polypeptide which catalyzes the phosphorylation of sphingosine to produce sphingosine-1-phosphate. In another aspect, at least one of said agents decreases the level of a nucleic acid encoding said polypeptide. In another aspect, the level of said polypeptide is decreased in said cell. In each of these aspects, the polypeptide is exemplified by a sphingosine kinase selected from the group consisting of sphingosine kinase 1 and sphingosine kinase 2.

In one aspect, at least one of said agents modulates the level or activity of a polypeptide which catalyzes the phosphorylation of sphingosine to produce sphingosine-1-phosphate. In another aspect, at least one of said agents decreases the level of a sphingosine kinase. In another aspect, at least one of said agents decreases the activity of a sphingosine kinase. In each of these aspects, the polypeptide is exemplified by a sphingosine kinase selected from the group consisting of sphingosine kinase 1 and sphingosine kinase 2.

A variety of compounds may be used as agents to decrease the activity of sphingosine kinase, although they may have other effects within a cell, targeting other polypeptides as well.

To block the SK activity, an inhibitor of SK or siRNA to decrease the level of SK may be employed. A non-limiting list of compounds which have been characterized to be specific inhibitors of SK is shown in Table 1.

TABLE 1

Specific Inhibitors of SK

| No. | Name | Reference |
|---|---|---|
| 1 | DMS (D-erythro-N,N-dimethylsphingosine) | (7, 36) |
| 2 | D,L-threo-dihydrosphingosine | (2) |
| 3 | N,N,N-trimethylsphingosine | (27) |
| 4 | (2R,3S,4E)-N-methyl-5-(4'-pentylphenyl)-2-aminopent-4-ene-1,3-diol | (28) |
| 5 | SKI-I (5-naphthalen-2-yl-2H-pyrazole-3-carboxylic acid (2-hydroxy-naphthalen-1-ylmethylene)-hydrazide) | (9) |
| 6 | SKI-II (4-[4-(4-Chloro-phenyl)-thiazol-2-ylamino]-phenol) | (9) |
| 7 | SKI-V (2-(3,4-Dihydroxy-benzylidene)-benzofuran-3-one) | (9) |
| 8 | 5C (2,2-dimethyl-45-(1-oxo-2-hexadecyn-1-yl)-1,1-dimethylethyl ester-3-oxazolidinecarboxylic acid) | (34) |
| 9 | ABC294640 | (10) |
| 10 | ABC294735 | (1) |
| 11 | ABC747080 | (16) |

In one aspect of the invention, the agent is selected from the group consisting of DMS (D-erythro-N,N-dimethylsphingosine); D,L-threo-dihydrosphingosine; N,N,N-trimethylsphingosine, (2R,3S,4E)-N-methyl-5-(4'-pentylphenyl)-2-aminopent-4-ene-1,3-diol; SKI-I (5-naphthalen-2-yl-2H-pyrazole-3-carboxylic acid (2-hydroxy-naphthalen-1-ylmethylene)-hydrazide); SKI-II (4-[4-(4-Chloro-phenyl)-thiazol-2-ylamino]-phenol); SKI-V (2-(3,4-Dihydroxy-benzylidene)-benzofuran-3-one); 5C (2,2-dimethyl-45-(1-oxo-2-hexadecyn-1-yl)-1,1-dimethylethyl ester-3-oxazolidinecarboxylic acid); ABC294640; ABC294735; and ABC747080. Other aspects include derivatives of these and related compounds, including acids, salts, enantiomers, mixtures of enantiomers, racemates, esters, amides, prodrugs, and active metabolites, thereof.

Another aspect of the invention relates to a method wherein at least one of said agents modulates the level of a nucleic acid encoding a polypeptide which catalyzes the conversion of sphingosine-1-phosphate to phosphoethanolamine and hexadecanal. In one aspect, at least one of said agents increases the level of a nucleic acid encoding said polypeptide. In another aspect, the level of said polypeptide is increased in said cell. In each of these aspects, said polypeptide is exemplified by sphingosine-1-phosphate lyase.

In one aspect, at least one of said agents modulates the level or activity of a polypeptide which catalyzes the conversion of sphingosine-1-phosphate to phosphoethanolamine and hexadecanal. In another aspect, at least one of said agents increases the level of said polypeptide. In another aspect, at least one of said agents increases the activity of said polypeptide. In each of these aspects, said polypeptide is exemplified by sphingosine-1-phosphate lyase.

Other aspects of the invention relate to compositions comprising the compounds or agents described above which modulate the level or activity of a protein involved in the synthesis or degradation of sphingosine-1-phosphate in a cell or in a subject. These include pharmaceutical compositions which comprise at least one active compound or agent in a pharmaceutically-acceptable solvent (aqueous or non-aqueous), optionally comprising a pharmaceutically-acceptable acid or combination of pharmaceutically acceptable acids. The solution can optionally be encapsulated in hard gelatin capsules or soft elastic gelatin capsules. The solution can optionally be granulated with a pharmaceutically-acceptable granulating agent.

The contributions of S1P-metabolizing enzymes, such as SPL and SK, on the cellular responses to influenza virus infection and methods of manipulating these and similar enzymes to modulate influenza virus replication and the virus-induced cytopathic effects are disclosed. Also disclosed is evidence demonstrating that overexpression of SPL interferes with influenza virus amplification and virus-induced cell death by enhancing the early activation of STAT1 and extracellular signal-regulated kinase (ERK) molecules. Evidence that the SK1-overexpressing cells (SK1-cells) are more susceptible to viral infection, produce increased amount of viral proteins and viral progeny, is also disclosed. Evidence that the suppression of SK1 blocks influenza virus replication both in vitro and in vivo is also disclosed. Evidence that influenza virus increases the amount and activation of SK1 is disclosed. Evidence that SK inhibitor blocks nuclear export of influenza virus NP by modulating RanBP3 activation and ERK signaling pathway is disclosed. Evidence that SK inhibitor interferes with measles virus replication is also disclosed.

In summary, sphingolipid balance, therefore, appears to play a key role in regulating host cell defense mechanisms directed against negative strand RNA virus infections. The pharmacological inhibition of SK and/or activation/overexpression of SPL blocks influenza virus propagation and infection-induced cytopathogenicity.

EXAMPLES

The foregoing discussion may be better understood in connection with the following representative examples, which are presented for purposes of illustrating the principle methods and compositions of the invention and not by way

Materials and Methods

All parts are by weight (e.g., % w/w), and temperatures are in degrees centigrade (° C.), unless otherwise indicated.

Virus and Cells

Influenza A/WSN/33 virus (H1N1) was provided by Yoshihiro Kawaoka (University of Wisconsin-Madison) and used in this study. To titrate virus, influenza virus-infected cells and supernatants containing released viruses were harvested at various times after infection. Viruses that were associated with cells were isolated by one or two cycles of freezing and thawing. Virus titer was determined on Madin-Darby Canine Kidney (MDCK) cells by a plaque assay method (36). HEK-cells and other established cell lines (SPL- and SK1-cells) were maintained as described previously (30, 31). Measles virus (Edmonston strain) was amplified and titrated on Vero cells, and used to infect B95-8 cells for virus production assay.

Western Blot Analysis

Specific antibodies against actin, influenza viral protein NP, NS1, NS2, M1, M2, Bax, Bcl-2, PARP, STAT1, pSTAT1, STAT2, pSTAT2, ERK, pERK, p38, p-p38, Akt, pAkt, JNK, pJNK, RanBP3, pRanBP3, p-p90RSK, and FLAG for SPL and SK1 were purchased from Cell Signaling Technology, Abcam, Upstate, or Santa Cruz Biotechnology. Total proteins were extracted by a RIPA buffer supplemented with inhibitors blocking proteases and phosphatases, and then normalized by using a Bradford assay. The protein samples (20 µg each) were run on a 12% SDS-PAGE gel and transferred to a PROTRAN-NC (Whatman). Membrane-bound antibodies were detected by enhanced chemiluminescence (Pierce). All of the presented data were repeated with independent experimental settings, at least twice.

RNA Interference

The siRNAs targeting SPL and RanBP3 was synthesized by Invitrogen Life Technologies and Qiagen respectively. siRNA used as a control (si-CTR) was purchased from Cell Signaling Technology. Cells were transfected with 10 nM (SPL) or 50 nM (RanBP3) siRNA using Lipofectamine RNAiMAX (Invitrogen Life Technologies) according to the manufacturer's instruction. Cells were then infected with influenza virus 3 days post-transfection. Knockdown of SPL or RanBP3 expression was verified by Western blot analysis. The experiment was independently-repeated twice, with similar results.

Inhibitor Assays

For the JAK inhibitor assay, HEK- and SPL-cells were uninfected or infected with influenza virus at 1 MOI. At 2 hpi, cells were treated with a solvent control (1% DMSO), JAK inhibitor I (2 or 10 µM), AG490 (inhibitor for JAK2, 2 µM), or JAK3 inhibitor I (2 µM) (Calbiochem). To inhibit STAT1 expression, HEK- and SPL-cells were pre-treated with fludarabine (1 µM) (Sigma) or its solvent control (1% DMSO) for 6 hr and then infected with influenza virus at 1 MOI. To inhibit SK activity, SK1-cells were pre-incubated with DMS (Cayman Chemical) or its solvent (1% DMSO) as a control for 3 hr and then infected with influenza virus. The results were confirmed by repeated experiments.

Sphingolipids

FTY720, D-erythro-sphingosine, and S1P were purchased from Cayman Chemicals. HEK-cells were infected with influenza virus and simultaneously treated with FTY720 (1 µM), D-erythro-sphingosine (1 µM), or its solvent (1% DMSO). Similarly, virus-infected cells were treated with S1P (1 µM) or its solvent (3 mM NaOH). These experiments were repeated two more times, with similar results.

Flow Cytometric Analysis

For detection of viral NP and Bax, HEK-, SPL-, or SK1-cells were uninfected or infected with influenza virus at 0.1 or 1 MOI. At 2 or 3 dpi, cells were incubated with anti-Bax and anti-viral NP antibodies for 1 hr and then stained with PE- and APC-conjugated secondary antibodies (BD) for 1 hr. Apoptotic cell death was detected by using an Annexin V-FITC apoptosis detection kit (BD Pharmingen) according to the manufacturer's instructions. Cells ($1 \times 10^5$) were washed twice with a cold phosphate buffered saline (PBS) and then incubated with Annexin V-FITC for 15 min at RT in the dark. Data were immediately collected by CyAn ADP flow cytometer (Beckman Coulter) and analyzed with FlowJo (Treestar) software. The data shown are representative of three independent experiments.

Immunocytochemistry

Cells were plated on four-well chamber slides (Nunc) and infected with influenza virus at 1 MOI. At 12 or 48 hpi, cells were fixed in 4% paraformaldehyde and then permeabilized in 0.5% Triton X-100 (Sigma) for 10 min. Cells were blocked in 1% BSA solution for 2 hr and then incubated with anti-Bax antibody (BD, clone 6A7) or anti-viral NP antibody (Abcam) overnight at 4° C. Cells were stained with Alexa Fluor 488-conjugated anti-mouse IgG and Alexa Fluor 546-conjugated anti-rabbit IgG for 2 hr and then incubated in DAPI solution (300 nM, Invitrogen). Images were obtained on a Zeiss LSM 510 META confocal microscopy. Representative fields are shown. Uninfected control images were selected from 5 different fields. Images for influenza virus-infected cells were chosen from over 10 fields. Results were equivalent in a repeat experiment.

Real-Time PCR

Total cellular RNA was purified by using Tri-reagent (Sigma-Aldrich) according to the manufacturer's description and treated with DNAse I to remove contaminated DNAs. Total RNA was reverse-transcribed, and the resulting cDNA was analyzed by real-time PCR using gene-specific primer sets. Primers for IFN-β (SEQ ID NOS: 1 and 2), GAPDH (SEQ ID NOS: 3 and 4), SK1 (SEQ ID NOS: 5 and 6), and SK2 (SEQ ID NOS 7 and 8) were used as shown in Table 2, below.

TABLE 2

Table of Primers

| Name | Description | Length | Type | SEQ ID NO: |
|---|---|---|---|---|
| IFN-fwd | CGC CGC ATT GAC CAT CTA | 18 | ssDNA | 1 |
| IFN-rev | GAC ATT AGC CAG GAG GTT CTC A | 22 | ssDNA | 2 |
| GAPDH-fwd | TCA CCA CCA TGG AGA AGG | 18 | ssDNA | 3 |
| GAPDH-rev | GAT AAG CAG TTG GTG GTG CA | 20 | ssDNA | 4 |
| SK1-fwd | TGT GAA CCA CTA TGC TGG GTA | 21 | ssDNA | 5 |
| SK1-rev | CAG CCC AGA AGC AGT GTG | 18 | ssDNA | 6 |
| SK2-fwd | AGA CGG GCT GCT TTA CGA G | 19 | ssDNA | 7 |
| SK2-rev | CAG GGG AGG ACA CCA ATG | 18 | ssDNA | 8 |

Quantitative real-time PCR reactions were performed with SYBR Green I chemistry using an ABI 7900 HT real time PCR instrument. The authenticity of the PCR products was verified by melting curve analysis. cDNA quantities were normalized to GAPDH RNA quantities measured in the same samples. The experiment was independently repeated twice, with similar results.

Statistical Analysis

All error bars represent the mean±SEM, and averages were compared using a bidirectional unpaired Student's t-test.

Example 1

SPL Overexpression Inhibits Influenza Virus Propagation

Refer to FIGS. 1A-1D. To investigate whether SPL affects influenza viral propagation, the HEK and SPL-cells were infected with influenza A/WSN/33 (WSN) virus at 0.1 MOI and then monitored for viral amplification. Viral titers were determined by a plaque assay at 6, 12, 24 or 48 hr post-infection (hpi) (left panel of FIG. 1(A)), and 3 or 4 days post-infection (dpi) (right panel of FIG. 1A). The virus produced its progeny on HEK-cells with a 10-fold increase of titer when assessed at 24 hpi, compared to SPL-cells at that time point (24 hpi) (FIG. 1A). The increase of viral titer over time was prominent with HEK-cells compared to SPL-cells. At 3 and 4 dpi, approximately 100-fold fewer viruses were produced from SPL-cells, when compared to the titer observed for HEK-cells. Increased SPL expression, therefore, strongly impaired the synthesis of influenza viral nucleoprotein (NP) in the cells as noted from data obtained by Western blot analysis (FIG. 1(B)). The number of NP-expressing cells [NP(+)] was strongly decreased in SPL-cells [NP(+) HEK-cells, 30%; NP(+) SPL-cells, 9%] (FIG. 1(C)) when they were assessed at 3 dpi. The mean fluorescence intensity (MFI) of NP(+) SPL-cells that represents the level of NP (MFI=88) was lower than that of NP(+) HEK-cells (MFI=100), which was observed in repeated experiments [12-28% decrease in the MFI of NP(+) SPL-cells compared to that of NP(+) HEK-cells]. These results suggest that SPL inhibits influenza virus replication, leading to the diminished production of virus particles that could infect neighboring cells.

To confirm the SPL-mediated inhibition of virus propagation, a small interfering (si) RNA approach was utilized. Specific siRNA targeting SPL effectively down-regulated the expression of SPL in SPL-cells. Consequently, the expression of viral NP (left panel of FIG. 1D) and viral titer (right panel of FIG. 1D) clearly increased, compared to that observed in non-specific siRNA (si-CTR) or mock-treated conditions. Taken together, these results demonstrate that overexpression of SPL inhibits the amplification of infectious influenza virus.

Example 2

Figure 2:
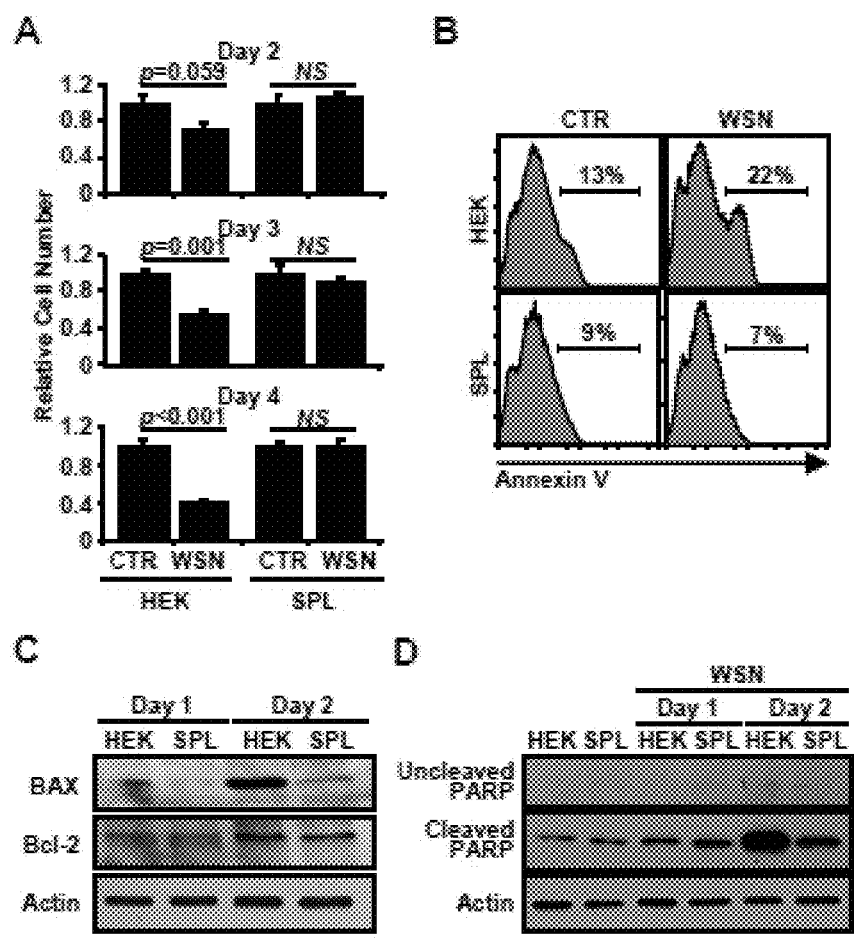
FIG. 2 (Panels A-D) set forth data illustrating the reduced cytopathic effects (CPEs) in influenza virus-infected SPL-cells. (A) HEK-cells or SPL-cells were uninfected (CTR) or infected with influenza virus at 1 MOI. At 2, 3 or 4 dpi, cellular viability was monitored by using a trypan blue exclusion assay. The number of uninfected cells was set as 1.0, and the relative numbers of virus-infected groups were compared. Three separate wells per group were used (n=3). Mean±SEM. p values are depicted in the figure to show statistical significance. NS indicates no significant difference. (B) HEK-cells or SPL-cells were uninfected or infected with influenza virus at 5 MOI. Cells were stained with Annexin V at 1 dpi and then analyzed by flow cytometry. Percentiles of Annexin V(+) cells are shown. (C and D) HEK-cells or SPL-cells were infected with influenza virus at 1 MOI. Cell lysates were used for Western blot analysis to detect Bax, Bcl-2 and actin (C), and uncleaved, cleaved PARP and actin (D) at 1 or 2 dpi.

SPL Overexpression Renders Cells Resistant to Influenza Virus-Induced Cytopathic Effect Refer to FIGS. 2A-2D. Influenza virus induces apoptosis in the infected cells (13, 31). As expected, the infection of HEK-cells with influenza virus caused apparent CPEs when the cells were analyzed at 2-4 dpi by using a Trypan blue exclusion assay (FIG. 2A) or visual inspection with phase-contrast microscopy. The viability of HEK-cells was strongly diminished by influenza virus infection (day 2, a 30% decrease; day 3, a 45% decrease; and day 4, a 59% decrease). SPL-cells were notably resistant to the influenza virus infection-induced CPEs, however, compared to the HEK-cells (FIG. 2A). The inhibition of virus-induced apoptosis by SPL was also observed when the cells were stained with a fluorescence-conjugated Annexin V, an early marker of cellular apoptosis, and then analyzed by flow cytometry (FIG. 2B).

The finding for SPL-mediated reduced CPEs upon influenza virus infection prompted us to define the underlying molecular mechanism. Recently, the activation of the pro-apoptotic protein Bax was reported to be critical for efficient induction of apoptosis caused by influenza virus through caspase activation (19). Therefore, the change of Bax level in influenza virus-infected cells was evaluated following the overexpression of SPL. After influenza virus infection, the Bax was up-regulated in HEK-cells over time (FIG. 2C). Overexpression of SPL strongly inhibited the virus-induced elevation of Bax expression. However, the expression of an anti-apoptotic protein Bcl-2 did not change (FIG. 2C). The activation of the apoptotic pathway downstream of Bax was further evaluated. Cleaved 84 kDa-sized form of PARP is known to be generated by activated caspase-3 (32) and increased by influenza virus infection (14, 22). In support of Bax regulation, the level of cleaved PARP markedly increased in HEK-cells at 2 dpi, but not in SPL-cells (FIG. 2D). Thus, SPL mediated profound suppression of Bax expression and PARP cleavage reflecting the increased viability of SPL-cells upon influenza virus infection.

Figure 3:
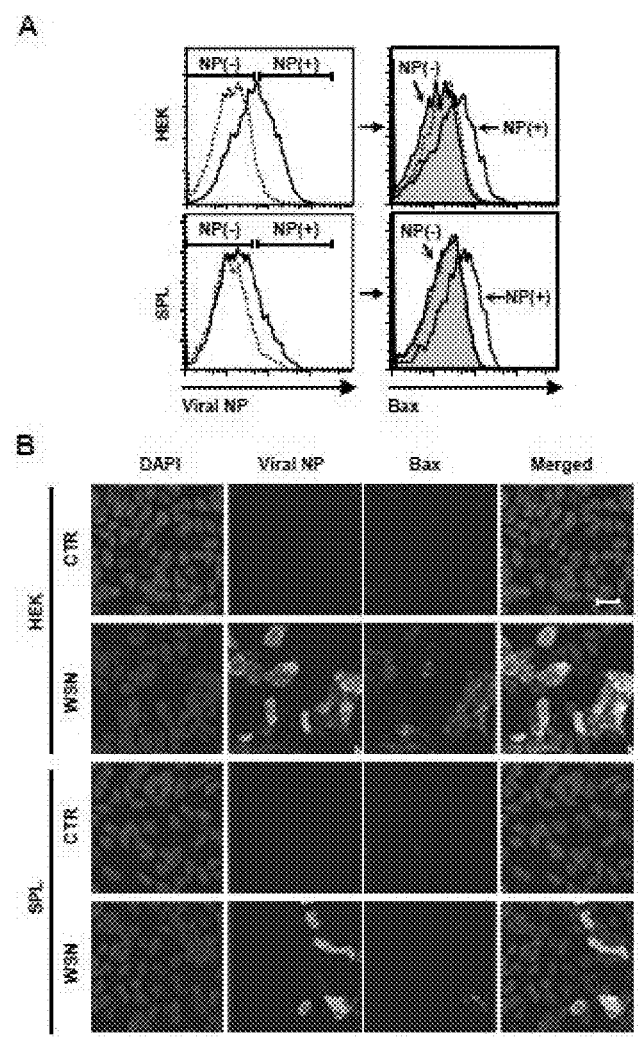
FIG. 3 (Panels A-B) set forth data illustrating co-expression of Bax and viral NP in influenza virus-infected HEK- or SPL-cells. (A) HEK-cells or SPL-cells were uninfected (dotted line) or infected (solid line) with influenza virus at 1 MOI, and then at 2 dpi, the expression of viral NP was assessed by flow cytometry (left panels). Virus-treated cells (solid line) in the left panels were separated into NP-expressing [NP(+)] and non-expressing [NP(−)] cells. Then, Bax expression of the NP(+) cells (solid line) and NP(−) cells (shaded) was compared with that of uninfected cells (dotted line) in the right panels. (B) Cells were uninfected (CTR) or infected with influenza virus at 1 MOI. They were fixed, permeabilized and stained with DAPI detecting nucleus and antibodies against viral NP and Bax at 2 dpi. Representative confocal images are shown (original magnification, 200×). White scale bar indicates 20 μm.

Refer to FIGS. 3A to 3B. Flow cytometric analysis was conducted to determine whether apoptosis is restricted to influenza virus-infected cells. As shown above, HEK-cells were more sensitive to the virus infection and displayed increased NP expression (left panels of FIG. 3A) and Bax expression than SPL-cells. In both HEK-cells and SPL-cells, some NP(+) cells were co-expressing Bax, while a majority of the NP(−) cells did not (right panels of FIG. 3A). Not all virus-infected NP(+) cells co-expressed Bax. One possible explanation is that at the early stage of influenza virus replication in the nucleus, the cells might not be undergoing apoptosis, and the virus-induced apoptosis is associated with the nuclear export of ribonucleoprotein complex of influenza virus (35). This was further confirmed by immunocytochemistry (FIG. 3B). NP(+) or Bax(+) cells were readily detectable in influenza virus-infected HEK-cells compared to the infected SPL-cells; most of Bax(+) cells were expressing viral NP simultaneously, complementing the results obtained using flow cytometry.

Example 3

Figure 4:
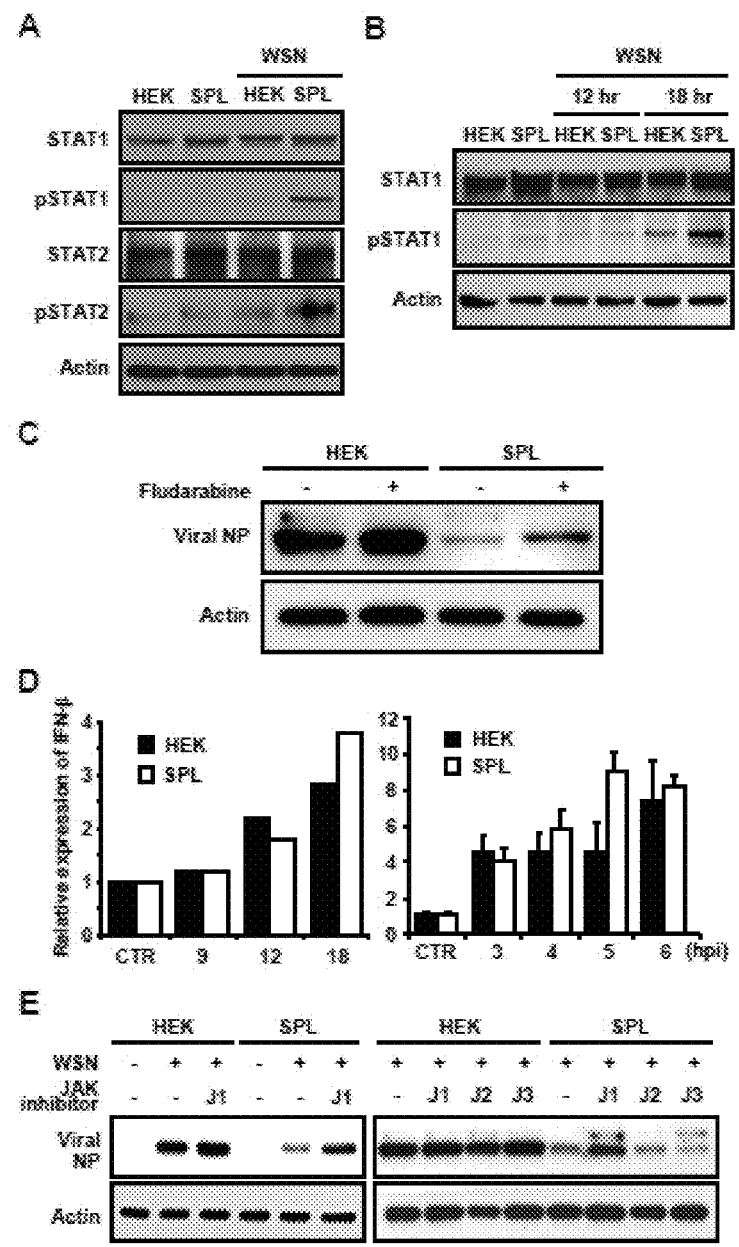
FIG. 4 (Panels A-E) set forth data illustrating the analyses for the activation of JAK/STAT following influenza virus infection of SPL-cells. HEK-cells or SPL-cells were uninfected or infected with influenza virus at 1 MOI. (A) At 1 dpi, cell lysates were used for Western blot analysis to detect STAT1, pSTAT1, STAT2, pSTAT2 and actin. (B) At 0, 12 or 18 hpi, whole proteins were extracted and then used for Western blot analysis to detect STAT1, pSTAT1 and actin. (C) HEK- or SPL-cells were pre-treated with fludarabine (1 μM) blocking STAT1 expression, and at 2 dpi, the expression of viral NP and actin was analyzed. (D) HEK-cells (filled bars) and SPL-cells (open bars) were uninfected (CTR) or infected with influenza virus at 1 MOI (left panel) or 10 MOI (right panel). Reverse transcription followed by quantitative real-time PCR was performed to detect the relative mRNA level of IFN-β. Three reactions per sample in the right panel (n=3), Mean±SEM. (E) HEK- or SPL-cells were treated with inhibitors for JAK1 (J1, 10 μM for left panel or 2 μM for right panel), JAK2 (J2, 2 μM), or JAK3 (J3, 2 μM) at 2 hpi. After 2 days, the level of viral NP and actin was assessed by Western blot analysis.

SPL Overexpression Induces the Activation of STAT1 and ERK1/2 Upon Influenza Virus Infection Refer to FIGS. 4A to 4E. Since STAT1/2 molecules are transcriptional activators essential for the type I interferon (IFN) signaling that induces the anti-viral state (11), their activation in HEK-cells and SPL-cells following infection by influenza virus was examined. Overexpression of SPL strongly increased expression of phosphorylated STAT1 (pSTAT1) and pSTAT2 was slightly up-regulated at 1 dpi (FIG. 4A). Further analysis revealed that the elevation of pSTAT1 occurred on SPL-cells between 12 and 18 hpi (FIG. 4B). When STAT1 expression was blocked by the inhibitor fludarabine, viral NP (FIG. 4C) and Bax (data not shown) were preferentially up-regulated in SPL-cells. STAT1, therefore appears to be an important cellular component for the inhibition of influenza virus replication and viral cytopathogenicity by SPLs. STAT1/2 activation, however, does not appear to be due to the increased type I IFN synthesis in SPL-cells, because the amounts of type I IFN at the level of mRNA did not change notably over time compared to experiments carried out using HEK-cells (FIG. 4D). As STAT1 and STAT2 are phosphorylated by non-receptor tyrosine kinases of the Janus kinase (JAK) 1 and Tyrosine kinase 2 (TYK2) in the type I IFN signaling, inhibitor studies blocking their kinase activities were performed to determine the involvement of JAK/STAT signal in the modulation of virus replication by SPLs. HEK-cells or SPL-cells which were uninfected or infected with influenza virus were then treated with a JAK1 inhibitor (JAK inhibitor I) that primarily blocks JAK1 activity and secondarily blocks JAK2, JAK3, and TYK2 activities. Inhibition of these kinase activities strongly elevated the expression level of viral NP in influenza virus-infected SPL-cells, whereas only a little increase of NP expression was detected in JAK1 inhibitor-treated HEK-cells (left panel of FIG. 4E). Contrasting results were obtained with inhibitors that specifically block the activation of JAK2 or JAK3, where the viral NP expression in SPL-cells did not increase (right panel of FIG. 4E). Taken together, these results indicate that the activation of STAT signaling pathway by JAK1/Tyk2 is critical for the suppression of influenza virus replication observed in SPL-cells.

Figure 5:
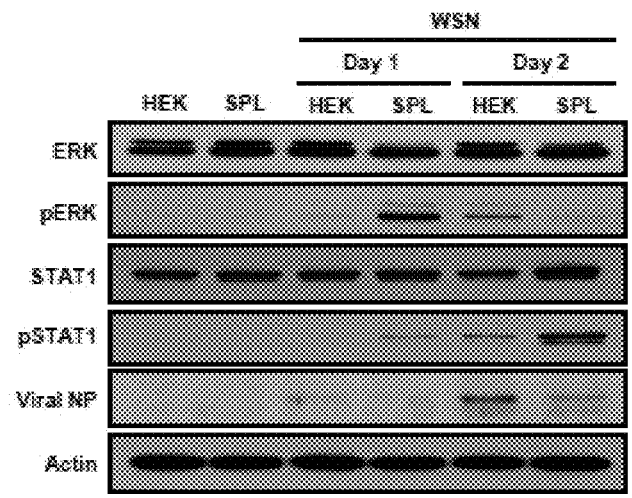
FIG. 5 (Panels A-B) set forth data illustrating the preferential activation of ERK, but not of p38, Akt, and JNK, in SPL-cells. HEK-cells or SPL-cells were uninfected or infected with influenza virus at 1 MOI. (A) At 1 or 2 dpi, whole proteins were used for Western blot analysis to record the expression of ERK, pERK, STAT1, pSTAT1, viral NP and actin. (B) Cell lysates were obtained at 1 or 2 dpi and analyzed by Western blotting to determine the levels of p38, p-p38, Akt, pAkt, JNK, pJNK and actin.
Figure 5:
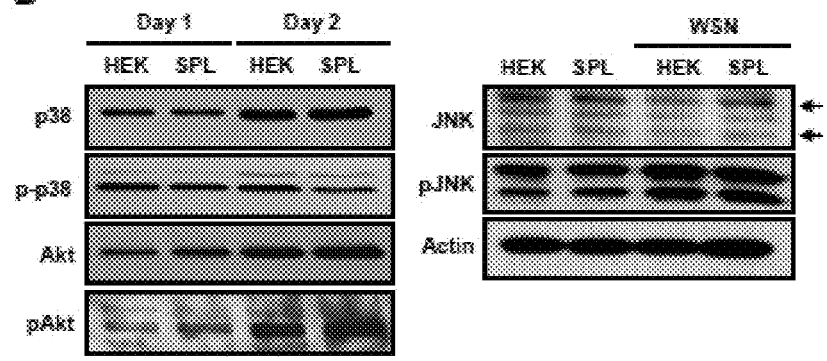

Refer to FIGS. 5A to 5B. In earlier studies, the increased sensitivity of SPL-cells to cisplatin was reported to be dependent on p38 mitogen-activated protein kinase (MAPK), and partly on c-Jun N-terminal kinase (JNK) signaling, but involve no activation of ERK (21). Involvement of these cellular pathways could affect the STAT signaling cascade. ERK2, for example, was reported to interact with STAT1 and type I IFN receptor (5).

In view of these observations, the activation of the diverse signaling molecules ERK, p38 MAPK, Akt, and JNK following the infection of SPL-cells with influenza virus was studied further. The virus strongly induced the activation of ERK1/2 (p44/p42 MAPK), particularly ERK2 (p42) and STAT1 in SPL-cells at 1 dpi, compared to their expression in HEK-cells (FIG. 5A). Unlike pSTAT1, the level of activated pERK quickly diminished in SPL-cells at 2 dpi when pERK was up-regulated in HEK-cells (FIG. 5A). The phosphorylation of p38 MAPK (p-p38), Akt (p-Akt) or JNK (p-JNK) was not significantly affected by influenza viral infection in SPL-cells compared to their results obtained using virus-infected HEK-cells (FIG. 5B). The activation of STAT1 and ERK, therefore, appears to be a specific early event occurring in SPL-cells following influenza virus infection.

Example 4

SK1 Increases the Susceptibility of Cells to Influenza Virus Infection

Figure 6:
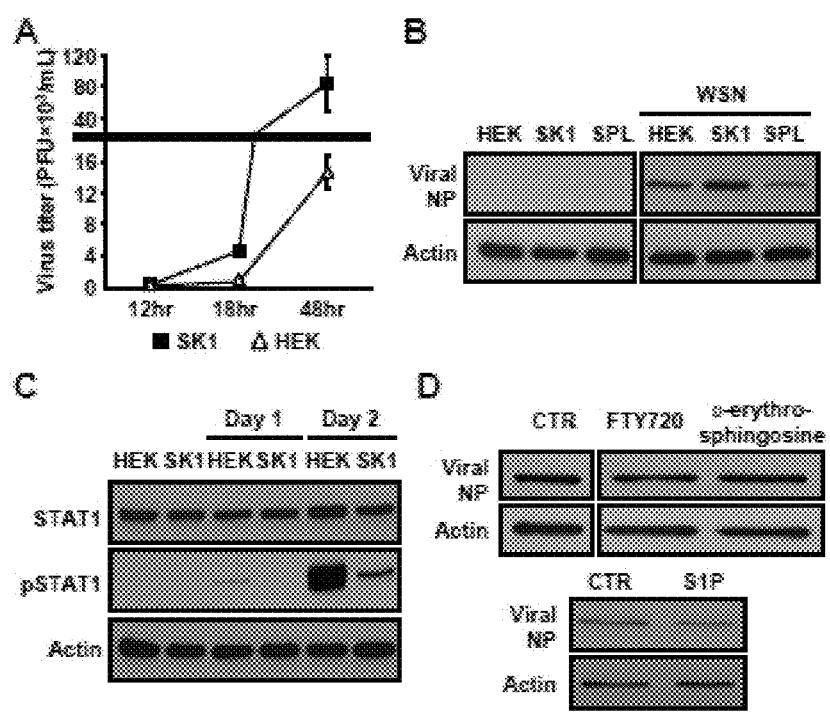
FIG. 6 (Panels A-D) set forth data illustrating the enhanced susceptibility of SK1-cells to influenza virus infection. (A) HEK-cells (open triangle) or SK1-cells (filled square) were infected with influenza virus at 0.1 MOI. At 12, 18 or 48 hpi, virus titers were determined by plaque assay. n=3 separate virus-infected cells per group at each time point; Mean±SEM. (B) Western blot analysis was conducted at 2 dpi to detect viral NP and actin. (C) Cell lysates were used for Western blot analysis to detect STAT1, pSTAT1 and actin. (D) HEK-cells were infected with influenza virus at 1 MOI and treated with solvent controls, FTY720 (1 μM), D-erythro-sphingosine (1 μM) or S1P (1 μM). At 2 dpi, total proteins were extracted to detect viral NP and actin by Western blot analysis.

Refer to FIGS. 6A to 6D. SK1 produces S1P via its kinase function, while S1P lyase induces the degradation of S1P (30). Experiments were performed to evaluate whether overexpression of SK1 affects influenza viral propagation differently from experiments where SPL-cells were used. Unlike results obtained in SPL-cells, SK1-overexpressing cells (SK1-cells) were more susceptible to viral infection than control HEK-cells (FIG. 6A). influenza virus-infected SK1-cells produced more progeny virus at 18 or 48 hpi than HEK-cells (FIG. 6A) and at 3 dpi (data not shown), and phenotypic death of the former cells was prominent by visual inspection with phase-contrast microscopy (data not shown). Viral protein expression was also greater in SK1-cells than in HEK-cells or SPL-cells, providing supporting evidence of increased viral replication in SK1-cells (FIG. 6B). pSTAT1 expression was also inhibited in the infected SK1-cells compared to HEK-cells (FIG. 6C). These findings strongly suggest that overexpression of SK1 increases the susceptibility of these cells to influenza virus infection, which correlates with observations relating to the suppression of STAT1 activation. Direct treatment of cells with a synthetic sphingosine analog FTY720, D-erythro-sphingosine or S1P, however, failed to enhance the synthesis of influenza viral NP (FIG. 6D). These results suggest that the increase of influenza virus replication is not mediated by S1P receptor signaling, but is regulated by SK1, presumably via intracellular S1P signaling or through an altered balance of sphingolipid-related compounds.

Example 5

Inhibition of SK's Enzymatic Action Reduces Susceptibility of Cells to Influenza Virus Infection
(In Vitro)

Figure 7:
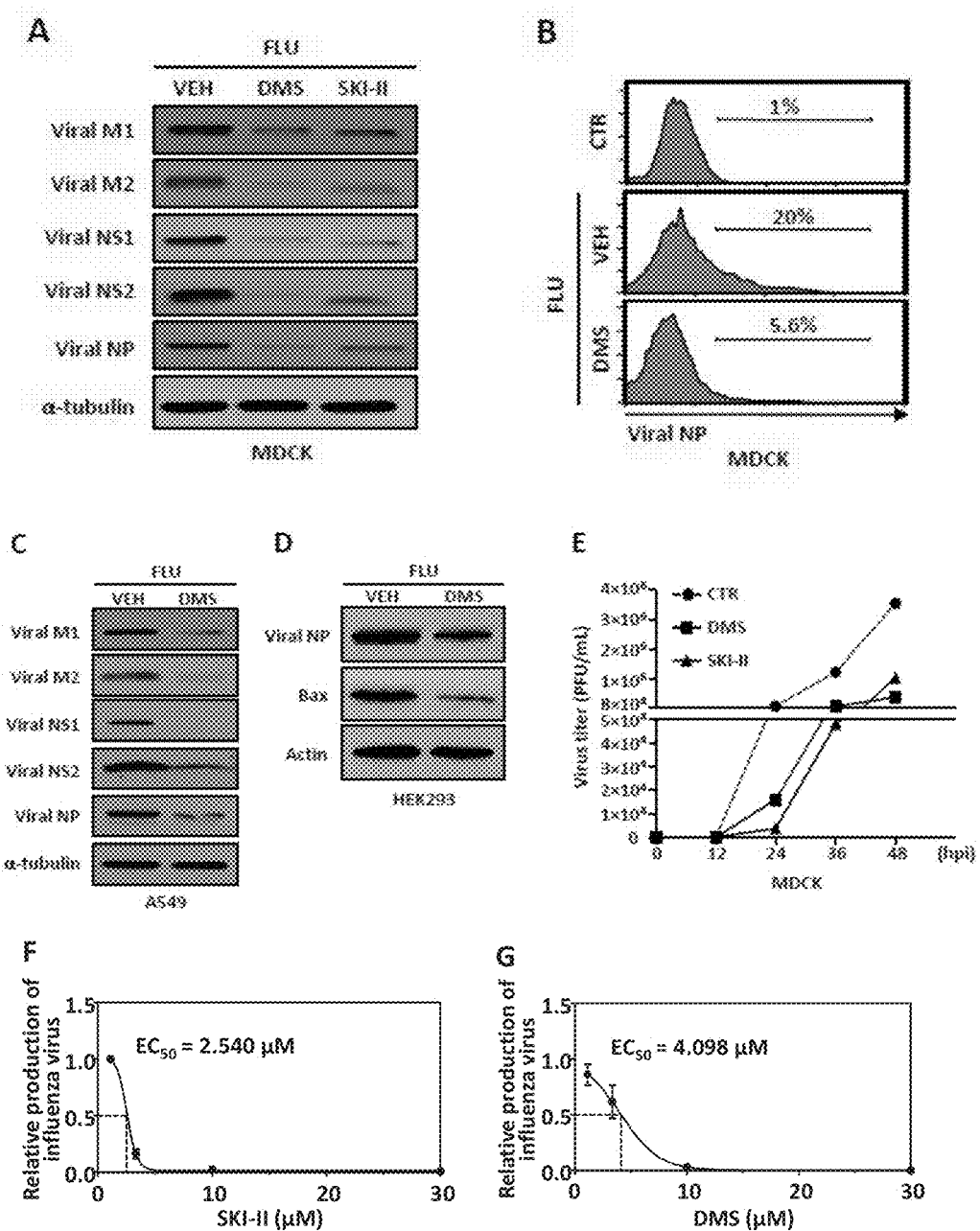
FIG. 7 (Panels A-G) set forth data illustrating suppressive activity of SK inhibitors in influenza virus replication. MDCK (A, B), A549 (C), or HEK293 (D) cells were infected with influenza virus at 1 MOI and treated with vehicle (VEH, solvent control), D-erythro-N,N-dimethyl-sphingosine (DMS) (5 μM), or (4-[[4-(4-chlorophenyl)-2-thiazolyl]amino]-phenol) (SKI-II) (10 μM). At 12 hpi (A, B, C) or 1 dpi (D), the expression of viral proteins was analyzed by Western blotting (viral M1, M2, NS1, NS2, and NP) or flow cytometry (viral NP). (E) MDCK cells were infected with influenza virus at 0.001 MOI and treated with VEH, DMS (5 μM), or SKI-II (10 μM). Infectious virus particles produced from the cells were titrated by using a plaque assay. (F, G) MDCK cells were infected with influenza virus at 0.1 MOI in the absence or presence of SKI-II (F) or DMS (1.1, 3.3, 10, or 30 μM) (G). At 24 hpi, virus titers were determined by using a plaque assay. Results represent the average of relative influenza virus production with error bars showing SEM of data obtained from each condition (n=3). The 50% efficacy concentration ($EC_{50}$) of SKI-II and DMS in blocking influenza virus production was determined by using GraphPad Prism.

Refer to FIGS. 7A to 7G. To determine if SK inhibitors impair influenza virus (WSN) replication and production, we carried out experiments using DMS and SKI-II. Both DMS and SKI-II inhibited influenza viral protein expression such as NP, NS1, NS2, M1, and M2 in MDCK cells (FIGS. 7A and 7B). The inhibition was also observed in HEK293 and A549 cells (FIGS. 7C and 7D). These two inhibitors also suppressed the production of infectious influenza virus particles from the cells when the virus titer was measured by a plaque assay method (FIG. 7E). SKI-II displayed a stronger activity to inhibit virus production with an $EC_{50}$ (50% efficacy concentration that blocks virus production) of 2.5 μM, than DMS, which had an $EC_{50}$ of 4.1 μM) (FIGS. 7F and 7G).

Example 6

Inhibition of SK's Enzymatic Action Reduces the Pathogenicity of Influenza (In Vivo)

Refer to FIGS. 8A and 8B. Wild-type C57BL/6 mice (n=5/group) were infected in vivo with influenza virus at $10^5$ PFU intra-nasally (i.n.) and injected with vehicle (CTR) or DMS {0.1 mg/kg (mpk)} and their lifespan was monitored. As shown in FIG. 8A, local injections of mice with a single dose of DMS (0.1 mpk) effectively protected them from influenza virus-induced death, although the mice lost ~20% of their weight at 9-10 dpi. Lower dose of DMS (0.012 mpk) also decreased the mortality rate of the infected mice (FIG. 8B). In a morbidity experiment, DMS administration significantly reduced the weight loss of the infected mice (n=5/group; −15% in CTR versus −7% in DMS-treated mice), supporting its beneficial effect. Similarly, local injections of mice with a single dose of SKI-II (0.012 mpk) increased viability of mice infected with influenza virus (FIG. 8B). The results indicate that the inhibition of SK reduces viral pathogenicity.

Example 7

Influenza Virus Increases Expression/Activity of SK1

Figure 9:
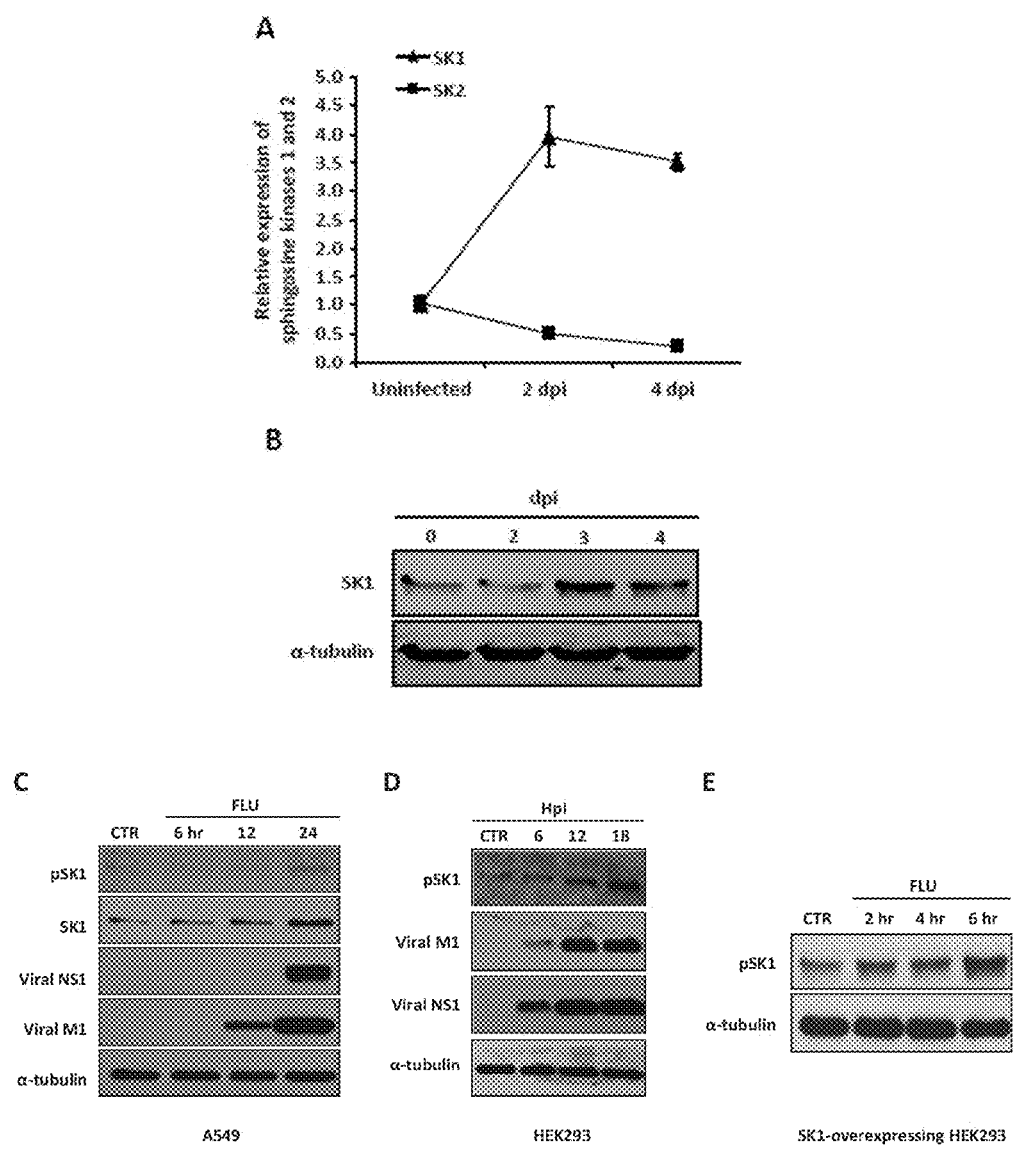
FIG. 9 (Panels A-E) set forth data illustrating increased expression/phosphorylation of SK1 by influenza virus infection. Mice were infected with $3 \times 10^5$ PFU of influenza virus intra-nasally. At the indicated time points, expression of sphingosine kinase (SK) 1 (A, B) and 2 (A) was analyzed by quantitative real-time PCR (A) or Western blotting (B). C-E, A549 (C), HEK293 (D), or SK1-overexpressing HEK293 (E) cells were infected with influenza virus at 1 MOI. At the indicated time points, the expression of proteins was analyzed by Western blotting.

Refer to FIGS. 9A and 9E. Since sphingosine kinase (SK) 1 increases the susceptibility of cells to influenza virus infection, we assessed whether influenza virus infection affects expression of SKs. Influenza virus infection increased the expression of SK1, but not SK2, in mouse lungs (FIGS. 9A and 9B). Further, the viral infection induced the activation of SK1 (phosphorylation of SK) in human lung epithelial cell line A549 (FIG. 9C), HEK293 (FIG. 9D), and SK1-overexpressing HEK293 cells (FIG. 9E).

Example 8

Figure 10:
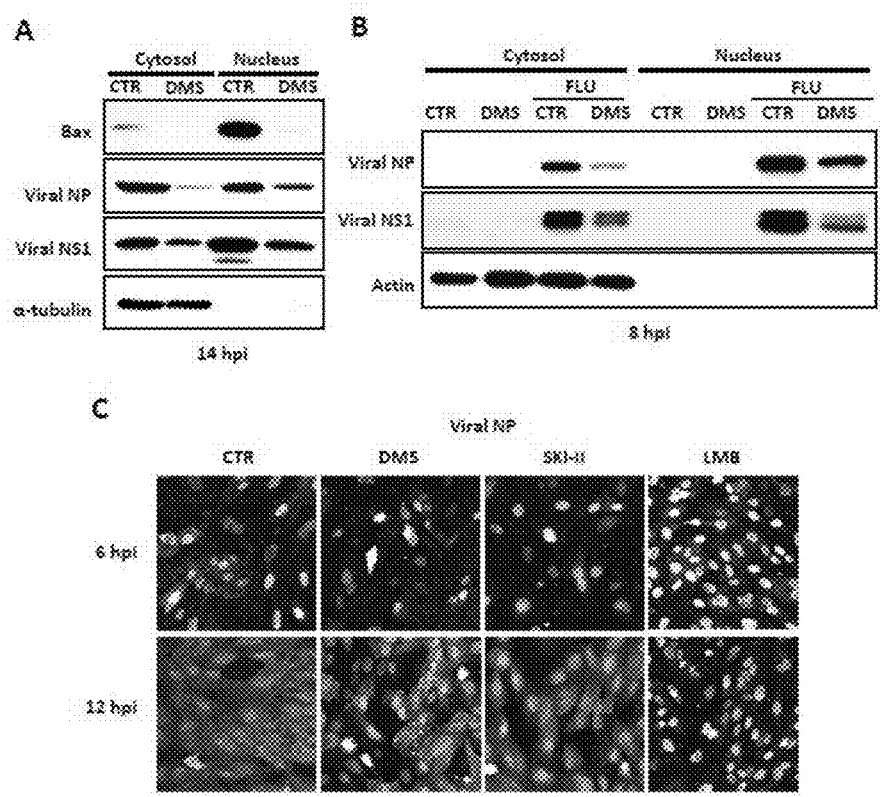
FIG. 10 (Panels A-C) set forth data illustrating impaired nuclear export of viral NP by SK inhibitor treatment. MDCK cells were left untreated or treated with DMS (5 μM) upon influenza virus infection (1 MOI). At 14 (A) or 8 hpi (B), the expression of Bax and viral proteins, NP and NS1, was detected in cytosol and nucleus by Western blotting. (C) MDCK cells were left untreated or treated with DMS (5 μM), SKI-II (10 μM), or Leptomycin B (LMB) for 6 or 12 hrs. Immunocytochemistry followed by confocal microscopic analysis was performed to detect influenza viral NP.

SK Inhibitor Impairs Nuclear Export of Viral RNP by Suppressing ERK Signaling and RanBP3 Activation Refer to FIGS. 10A and 10C. Nuclear export of influenza viral ribonucleoprotein (RNP) is also known to be critical for the viral replication production. We carried out experiments designed to evaluate the effect of an SK inhibitor on the localization of viral NP. Experiments involving fractionation analysis that separately evaluates the level of NP in nucleus and cytoplasm in Western Blot analysis (FIGS. 10A and 10B) and immunocytochemistry experiments involving confocal microscopic analysis (FIG. 10C) demonstrated that SK inhibition strongly impaired the nuclear export of NP and decreased the relative expression of NP in cytoplasm. The relative level of expression of the viral NS1 protein did not change, demonstrating the specific impairment of NP translocation by the SK inhibitor (FIGS. 10A and 10B). Similar inhibition of NP was also observed when S1P lyase was overexpressed in the cells, supporting the idea that SK inhibition and S1P lyase expression both inhibit influenza virus replication by modulating the nuclear export of influenza viral RNPs. The nuclear export of influenza virus RNP also appears to be mediated by CRM1 function, which was demonstrated treating cells with the CRM1 inhibitor, leptomycin B (FIG. 10C).

Figure 11:
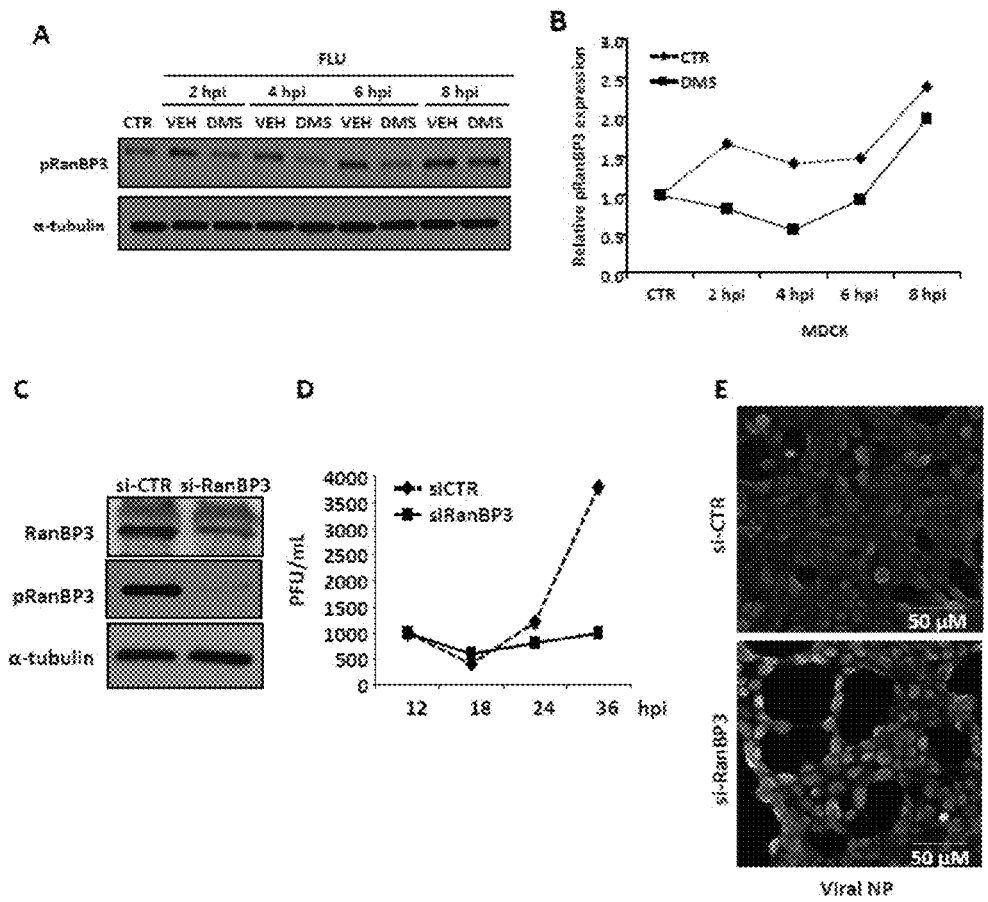
FIG. 11 (Panels A-E) set forth data illustrating critical role of RanBP3 in influenza virus replication and RanBP3 regulation by SK inhibitor. (A-B) MDCK cells were infected with influenza virus at 5 MOI and treated with VEH or DMS (5 μM). Cell lysates were obtained at the indicated time points and the expression of pRanBP3 was assessed by Western blot analysis. Relative expression of pRanBP3 is shown in panel B. (C-E) HEK293 cells were transfected with control siRNA (siCTR) or siRNA targeting RanBP3 (siRanBP3). Western blotting was performed to detect RanBP3 and pRanBP3 (C). Cells were transfected with siRNA and then infected with influenza virus at 0.001 MOI. Virus titers were determined by using a plaque assay (D). Cells were transfected with siRNA and then infected with influenza virus at 1 MOI for 12 hrs. Immunocytochemistry followed by confocal microscopic analysis was performed to detect influenza viral NP (E).

Refer to FIGS. 11A and 11E. We also found that influenza virus induced the activation of RanBP3, which is a known cofactor of CRM1 (15). DMS treatment blocked influenza virus-induced phosphorylation of RanBP3 (FIGS. 11A and 11B). A small interfering RNA (siRNA) approach was also used to test the role of RanBP3 in influenza virus replication. Expression and activation of RanBP3 was substantially impaired in cells transfected with a RanBP3-specific siRNA (si-RanBP3) (FIG. 11C). Blocking activation of RanBP3 inhibited the production of infectious influenza viruses from the cells (FIG. 11D). Nuclear export of viral NP was also inhibited by si-RanBP3, when analyzed by an immunocytochemistry method (FIG. 11E). Taken together, these results indicate that SK inhibition interferes with regulation of RanBP3 activation by influenza virus.

Figure 12:
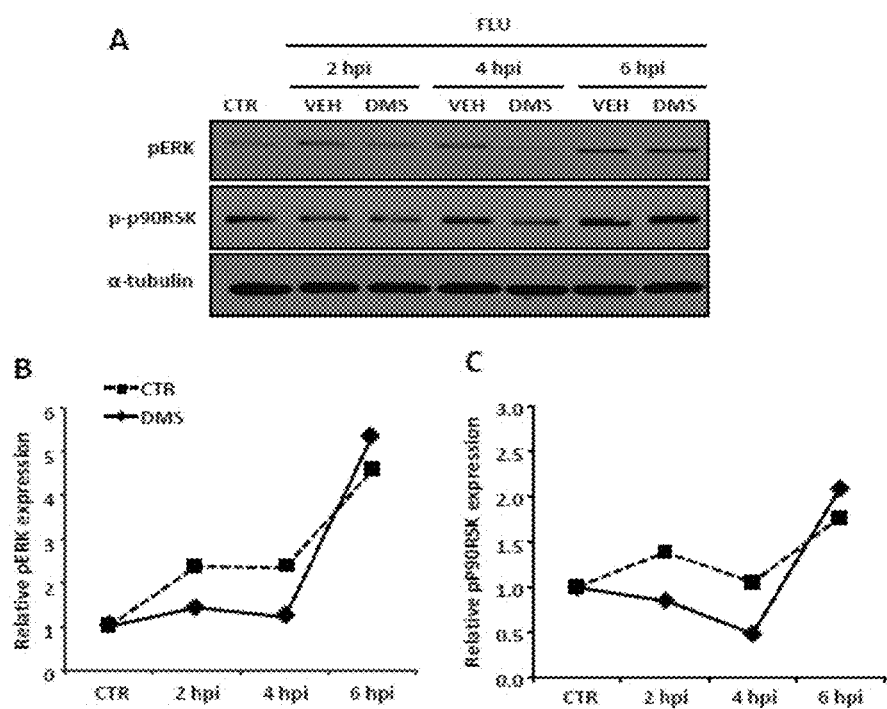
FIG. 12 (Panels A-C) set forth data illustrating reduced activation of ERK MAP kinase signal by SK inhibitor treatment upon influenza virus infection. (A). MDCK cells were treated with VEH or DMS (5 μM) and infected with influenza virus at 3 MOI. Cell lysates were obtained at the indicated time points and the expression of ERK MAP kinase signaling components were assessed by Western blot analysis. Relative expression of pERK and p90RSK is shown in panels B and C respectively (dotted line, VEH treated; solid line, DMS treated).

Refer to FIGS. 12A and 12C. The cellular enzyme p90RSK, which is a downstream kinase of ERK MAPK signaling pathway, has been shown to activate RanBP3 (37). To extend our observations, we evaluated the activation (phosphorylation) of p90RSK and ERK proteins in cells infected with virus or treated with DMS. DMS was observed to suppress influenza virus-induced activation of both p90RSK and ERK (FIG. 12). These results demonstrate that the SK inhibitor down-modulates influenza virus-induced ERK signaling pathway.

Example 9

SK Inhibitor Suppresses Measles Virus Replication

Refer to FIG. 13. To extend our observations to other negative strand RNA viruses, we carried out experiments to see if an SK inhibitor affected the replication of measles virus that belongs to Paramyxoviridae family. B95-8 cells were infected with measles virus at 1 MOI in the presence or absence of SKI-II (5 or 10 μM). SKI-II interfered with the production of measles virus from B95-8 cells at 2 or 3 days post-infection (dpi) (FIG. 13). The inhibition seems to be concentration-dependent, and expression of viral proteins was also inhibited by the inhibitor treatment (not shown). The results indicate that inhibition of SK suppresses viral replication in measles or influenza virus-infected cells.

While the specific examples and aspects of the invention have been illustrated and described in detail, it will be appreciated by those skilled in the art that that various changes can be made therein without departing from the spirit and scope of the disclosure. Accordingly, the particular arrangements disclosed are meant to be illustrative only, and not limiting as to the scope of the invention, which is to be given the full breadth of the appended claims and any equivalent thereof.

REFERENCES

All references, patents, or applications cited herein are incorporated by reference in their entirety, as if written herein.

1. Beljanski, V., C. Knaak, Y. Zhuang, and C. D. Smith. 2011. Combined anticancer effects of sphingosine kinase inhibitors and sorafenib. *Invest New Drugs* 29:1132-42.
2. Buehrer, B. M., and R. M. Bell. 1992. Inhibition of sphingosine kinase in vitro and in platelets. Implications for signal transduction pathways. *J Biol Chem* 267:3154-9.
3. Claas, E. C., A. D. Osterhaus, R. van Beek, J. C. De Jong, G. F. Rimmelzwaan, D. A. Senne, S. Krauss, K. F. Shortridge, and R. G. Webster. 1998. Human influenza A H5N1 virus related to a highly pathogenic avian influenza virus. *Lancet* 351:472-7.
4. Cyster, J. G. 2005. Chemokines, sphingosine-1-phosphate, and cell migration in secondary lymphoid organs. *Annu Rev Immunol* 23:127-59.
5. David, M., E. Petricoin, 3rd, C. Benjamin, R. Pine, M. J. Weber, and A. C. Larner. 1995. Requirement for MAP kinase (ERK2) activity in interferon alpha- and interferon beta-stimulated gene expression through STAT proteins. *Science* 269:1721-3.
6. Dharan, N. J., L. V. Gubareva, J. J. Meyer, M. Okomo-Adhiambo, R. C. McClinton, S. A. Marshall, K. St George, S. Epperson, L. Brammer, A. I. Klimov, J. S. Bresee, and A. M. Fry. 2009. Infections with oseltamivir-resistant influenza A(H1N1) virus in the United States. *JAMA* 301:1034-41.
7. Edsall, L. C., J. R. Van Brocklyn, O. Cuvillier, B. Kleuser, and S. Spiegel. 1998. N,N-Dimethylsphingosine is a potent competitive inhibitor of sphingosine kinase but not of protein kinase C: modulation of cellular levels of sphingosine 1-phosphate and ceramide. *Biochemistry* 37:12892-8.
8. Fraser, C., C. A. Donnelly, S. Cauchemez, W. P. Hanage, M. D. Van Kerkhove, T. D. Hollingsworth, J. Griffin, R. F. Baggaley, H. E. Jenkins, E. J. Lyons, T. Jombart, W. R. Hinsley, N. C. Grassly, F. Balloux, A. C. Ghani, N. M. Ferguson, A. Rambaut, O. G. Pybus, H. Lopez-Gatell, C. M. Alpuche-Aranda, I. B. Chapela, E. P. Zavala, D. M. Guevara, F. Checchi, E. Garcia, S. Hugonnet, and C. Roth. 2009. Pandemic potential of a strain of influenza A (H1N1): early findings. *Science* 324:1557-61.
9. French, K. J., R. S. Schrecengost, B. D. Lee, Y. Zhuang, S. N. Smith, J. L. Eberly, J. K. Yun, and C. D. Smith. 2003. Discovery and evaluation of inhibitors of human sphingosine kinase. *Cancer Res* 63:5962-9.
10. French, K. J., Y. Zhuang, L. W. Maines, P. Gao, W. Wang, V. Beljanski, J. J. Upson, C. L. Green, S. N. Keller, and C. D. Smith. Pharmacology and antitumor activity of ABC294640, a selective inhibitor of sphingosine kinase-2. 2010. *J Pharmacol Exp Ther* 333:129-39.
11. Garcia-Sastre, A., R. K. Durbin, H. Zheng, P. Palese, R. Gertner, D. E. Levy, and J. E. Durbin. 1998. The role of interferon in influenza virus tissue tropism. *J Virol* 72:8550-8.
12. Horga, A., and X. Montalban. 2008. FTY720 (fingolimod) for relapsing multiple sclerosis. *Expert Rev Neurother* 8:699-714.
13. Kash, J. C., T. M. Tumpey, S. C. Proll, V. Carter, O. Perwitasari, M. J. Thomas, C. F. Basler, P. Palese, J. K. Taubenberger, A. Garcia-Sastre, D. E. Swayne, and M. G. Katze. 2006. Genomic analysis of increased host immune and cell death responses induced by 1918 influenza virus. *Nature* 443:578-81.
14. Lin, C., R. E. Holland, Jr., J. C. Donofrio, M. H. McCoy, L. R. Tudor, and T. M. Chambers. 2002. Caspase activation in equine influenza virus induced apoptotic cell death. *Vet Microbiol* 84:357-65.
15. Lindsay, M. E., J. M. Holaska, K. Welch, B. M. Paschal, and I. G. Macara. 2001. Ran-binding protein 3 is a cofactor for Crm1-mediated nuclear protein export. *J Cell Biol* 153:1391-402.
16. Maines, L. W., L. R. Fitzpatrick, K. J. French, Y. Zhuang, Z. Xia, S. N. Keller, J. J. Upson, and C. D. Smith. 2008. Suppression of ulcerative colitis in mice by orally available inhibitors of sphingosine kinase. *Dig Dis Sci* 53:997-1012.
17. Marsolais, D., B. Hahm, K. H. Edelmann, K. B. Walsh, M. Guerrero, Y. Hatta, Y. Kawaoka, E. Roberts, M. B. Oldstone, and H. Rosen. 2008. Local not systemic modulation of dendritic cell S1P receptors in lung blunts virus-specific immune responses to influenza. *Mol Pharmacol* 74:896-903.
18. Marsolais, D., B. Hahm, K. B. Walsh, K. H. Edelmann, D. McGavern, Y. Hatta, Y. Kawaoka, H. Rosen, and M. B. Oldstone. 2009. A critical role for the sphingosine analog AAL-R in dampening the cytokine response during influenza virus infection. *Proc Natl Acad Sci USA* 106:1560-5.
19. McLean, J. E., E. Datan, D. Matassov, and Z. F. Zakeri. 2009. Lack of Bax prevents influenza A virus-induced apoptosis and causes diminished viral replication. *J Virol* 83:8233-46.
20. Min, J., A. Mesika, M. Sivaguru, P. P. Van Veldhoven, H. Alexander, A. H. Futerman, and S. Alexander. 2007. (Dihydro)ceramide synthase 1 regulated sensitivity to cisplatin is associated with the activation of p38 mitogen-activated protein kinase and is abrogated by sphingosine kinase 1. *Mol Cancer Res* 5:801-12.
21. Min, J., P. P. Van Veldhoven, L. Zhang, M. H. Hanigan, H. Alexander, and S. Alexander. 2005. Sphingosine-1-phosphate lyase regulates sensitivity of human cells to select chemotherapy drugs in a p38-dependent manner. *Mol Cancer Res* 3:287-96.
22. Mok, C. K., D. C. Lee, C. Y. Cheung, M. Peiris, and A. S. Lau. 2007. Differential onset of apoptosis in influenza A virus H5N1- and H1N1-infected human blood macrophages. *J Gen Virol* 88:1275-80.
23. Molinari, N. A., I. R. Ortega-Sanchez, M. L. Messonnier, W. W. Thompson, P. M. Wortley, E. Weintraub, and C. B. Bridges. 2007. The annual impact of seasonal influenza in the US: measuring disease burden and costs. *Vaccine* 25:5086-96.
24. Morens, D. M., and A. S. Fauci. 2007. The 1918 influenza pandemic: insights for the 21st century. *J Infect Dis* 195:1018-28.
25. Olivera, A., T. Kohama, L. Edsall, V. Nava, O. Cuvillier, S. Poulton, and S. Spiegel. 1999. Sphingosine kinase expression increases intracellular sphingosine-1-phosphate and promotes cell growth and survival. *J Cell Biol* 147:545-58.
26. Oskouian, B., P. Sooriyakumaran, A. D. Borowsky, A. Crans, L. Dillard-Telm, Y. Y. Tam, P. Bandhuvula, and J. D. Saba. 2006. Sphingosine-1-phosphate lyase potentiates apoptosis via p53- and p38-dependent pathways and is down-regulated in colon cancer. *Proc Natl Acad Sci USA* 103:17384-9.
27. Park, Y. S., S. Hakomori, S. Kawa, F. Ruan, and Y. Igarashi. 1994. Liposomal N,N,N-trimethylsphingosine (TMS) as an inhibitor of B16 melanoma cell growth and metastasis with reduced toxicity and enhanced drug efficacy compared to free TMS: cell membrane signaling as a target in cancer therapy III. *Cancer Res* 54:2213-7.
28. Paugh, S. W., B. S. Paugh, M. Rahmani, D. Kapitonov, J. A. Almenara, T. Kordula, S. Milstien, J. K. Adams, R. E. Zipkin, S. Grant, and S. Spiegel. 2008. A selective sphingosine kinase 1 inhibitor integrates multiple molecular therapeutic targets in human leukemia. *Blood* 112: 1382-91.

29. Rosen, H., and E. J. Goetzl. 2005. Sphingosine 1-phosphate and its receptors: an autocrine and paracrine network. *Nat Rev Immunol* 5:560-70.

30. Spiegel, S., and R. Kolesnick. 2002. Sphingosine 1-phosphate as a therapeutic agent. *Leukemia* 16:1596-602.

31. Takizawa, T., S. Matsukawa, Y. Higuchi, S. Nakamura, Y. Nakanishi, and R. Fukuda. 1993. Induction of programmed cell death (apoptosis) by influenza virus infection in tissue culture cells. *J Gen Virol* 74 (Pt 11):2347-55.

32. Tewari, M., L. T. Quan, K. O'Rourke, S. Desnoyers, Z. Zeng, D. R. Beidler, G. G. Poirier, G. S. Salvesen, and V. M. Dixit. 1995. Yama/CPP32 beta, a mammalian homolog of CED-3, is a CrmA-inhibitable protease that cleaves the death substrate poly(ADP-ribose) polymerase. *Cell* 81:801-9.

33. Thompson, W. W., D. K. Shay, E. Weintraub, L. Brammer, C. B. Bridges, N. J. Cox, and K. Fukuda. 2004. Influenza-associated hospitalizations in the United States. *JAMA* 292:1333-40.

34. Wong, L., S. S. Tan, Y. Lam, and A. J. Melendez. 2009. Synthesis and evaluation of sphingosine analogues as inhibitors of sphingosine kinases. *J Med Chem* 52:3618-26.

35. Wurzer, W. J., O. Planz, C. Ehrhardt, M. Giner, T. Silberzahn, S. Pleschka, and S. Ludwig. 2003. Caspase 3 activation is essential for efficient influenza virus propagation. *EMBO J* 22:2717-28.

36. Yatomi, Y., F. Ruan, T. Megidish, T. Toyokuni, S. Hakomori, and Y. Igarashi. 1996. N,N-dimethylsphingosine inhibition of sphingosine kinase and sphingosine 1-phosphate activity in human platelets. *Biochemistry* 35:626-33.

37. Yoon, S. O., S. Shin, Y. Liu, B. A. Ballif, M. S. Woo, S. P. Gygi, and J. Blenis. 2008. Ran-binding protein 3 phosphorylation links the Ras and PI3-kinase pathways to nucleocytoplasmic transport. *Mol Cell* 29:362-75.

What is claimed is:

1. A method of inhibiting the production of a negative-strand RNA virus in a eukaryotic cell, comprising administering a composition comprising one or more agents which modulate the level or activity of a polypeptide involved in the synthesis or degradation of sphingosine-1-phosphate in said cell, wherein said negative-strand RNA virus is in a family selected from the group consisting of Orthomyxoviridae, Paramyxoviridae, Rhabdoviridae, Filoviridae, Bornaviridae, and Bunyaviridae.

2. The method of claim 1, wherein at least one agent of said composition modulates the activity of a polypeptide which catalyzes the phosphorylation of sphingosine to produce sphingosine-1-phosphate.

3. The method of claim 2, wherein said polypeptide is sphingosine kinase.

4. The method of claim 3, wherein the sphingosine kinase is selected from the group consisting of sphingosine kinase 1 and sphingosine kinase 2.

5. The method of claim 2, wherein at least one of said agents decreases the activity of a sphingosine kinase.

6. The method of claim 5, wherein the sphingosine kinase is selected from the group consisting of sphingosine kinase 1 and sphingosine kinase 2.

7. The method of claim 5, wherein said agent is the compound SKI-II (4-[4-(4-Chloro-phenyl)-thiazol-2-ylamino]-phenol); and derivatives of this compound, including acids, salts, enantiomers, mixtures of enantiomers, racemates, esters, amides, prodrugs, and active metabolites, thereof.

8. The method of claim 1, wherein at least one agent of said composition modulates the activity of a polypeptide which catalyzes the conversion of sphingosine-1-phosphate to phosphoethanolamine and hexadecanal.

9. The method of claim 8, wherein at least one of said agents increases the activity of said polypeptide.

10. The method of claim 8, wherein said polypeptide is sphingosine-1-phosphate lyase.

11. A composition for inhibiting the production of a negative-strand RNA virus in a eukaryotic cell, comprising an effective amount of an S1P-modulating agent, wherein the S1P-modulating agent decreases the level of S1P within said cell in a sample of cells contacted with the S1P-modulating agent compared to control sample of cells not contacted with the S1P-modulating agent, wherein said negative-strand RNA virus is in a family selected from the group consisting of Orthomyxoviridae, Paramyxoviridae, Rhabdoviridae, Filoviridae, Bornaviridae, and Bunyaviridae.

12. The composition of claim 11, wherein at least one of said agents modulates the activity of a polypeptide which catalyzes the phosphorylation of sphingosine to produce sphingosine-1-phosphate.

13. The composition of claim 12, wherein said polypeptide is sphingosine kinase.

14. The composition of claim 13, wherein the sphingosine kinase is selected from the group consisting of sphingosine kinase 1 and sphingosine kinase 2.

15. The composition of claim 12, wherein at least one of said agents decreases the activity of a sphingosine kinase.

16. The composition of claim 15, wherein the sphingosine kinase is selected from the group consisting of sphingosine kinase 1 and sphingosine kinase 2.

17. The composition of claim 15, wherein said agent is the compound SKI-II (4-[4-(4-Chloro-phenyl)-thiazol-2-ylamino]-phenol); and derivatives of this compound, including acids, salts, enantiomers, mixtures of enantiomers, racemates, esters, amides, prodrugs, and active metabolites, thereof.

18. The composition of claim 11, wherein at least one of said agents modulates the activity of a polypeptide which catalyzes the conversion of sphingosine-1-phosphate to phosphoethanolamine and hexadecanal.

19. The composition of claim 18, wherein at least one of said agents increases the activity of said polypeptide.

20. The composition of claim 18, wherein said polypeptide is sphingosine-1-phosphate lyase.

21. A method for treating, preventing, or ameliorating one or more symptoms associated with a negative-strand RNA virus infection in a subject, said method comprising administering to said subject in need thereof, a prophylactically- or therapeutically-effective amount of a composition comprising one or more agents which modulate the level or activity of a polypeptide involved in the synthesis or degradation of sphingosine-1-phosphate in said subject, wherein said negative-strand RNA virus is in a family selected from the group consisting of Orthomyxoviridae, Paramyxoviridae, Rhabdoviridae, Filoviridae, Bornaviridae, and Bunyaviridae.

22. The method of claim 21, wherein at least one agent of said composition modulates the activity of a polypeptide which catalyzes the phosphorylation of sphingosine to produce sphingosine-1-phosphate.

23. The method of claim 22, wherein said polypeptide is sphingosine kinase.

24. The method of claim 23, wherein the sphingosine kinase is selected from the group consisting of sphingosine kinase 1 and sphingosine kinase 2.

25. The method of claim 22, wherein at least one of said agents decreases the activity of a sphingosine kinase.

26. The method of claim 25, wherein the sphingosine kinase is selected from the group consisting of sphingosine kinase 1 and sphingosine kinase 2.

27. The method of claim 25, wherein said agent is the compound SKI-II (4-[4-(4-Chloro-phenyl)-thiazol-2-ylamino]-phenol); and derivatives of this compound, including acids, salts, enantiomers, mixtures of enantiomers, racemates, esters, amides, prodrugs, and active metabolites, thereof.

28. The method of claim 21, wherein at least one agent of said composition modulates the activity of a polypeptide which catalyzes the conversion of sphingosine-1-phosphate to phosphoethanolamine and hexadecanal.

29. The method of claim 28, wherein at least one of said agents increases the activity of said polypeptide.

30. The method of claim 28, wherein said polypeptide is sphingosine-1-phosphate lyase.

\* \* \* \* \*

UNITED STATES PATENT AND TRADEMARK OFFICE
CERTIFICATE OF CORRECTION

PATENT NO. : 9,687,477 B2
APPLICATION NO. : 14/122399
DATED : June 27, 2017
INVENTOR(S) : Bumsuk Hahm et al.

It is certified that error appears in the above-identified patent and that said Letters Patent is hereby corrected as shown below:

On the Title Page

The first and last name of the fourth inventor should read:
"Madhuvanthi Vijayan"

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*